United States Patent
Lant et al.

(10) Patent No.: US 11,248,194 B2
(45) Date of Patent: *Feb. 15, 2022

(54) CLEANING COMPOSITIONS COMPRISING ENZYMES

(71) Applicant: The Procter & Gamble Company, Cincinnati, OH (US)

(72) Inventors: Neil Joseph Lant, Newcastle upon Tyne (GB); Katherine Esther Latimer, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/816,416

(22) Filed: Mar. 12, 2020

(65) Prior Publication Data
US 2020/0299620 A1 Sep. 24, 2020

(30) Foreign Application Priority Data
Mar. 14, 2019 (EP) .................................... 19162993

(51) Int. Cl.
| C12N 9/24 | (2006.01) |
|---|---|
| C11D 3/386 | (2006.01) |
| C11D 1/22 | (2006.01) |
| C11D 1/29 | (2006.01) |

(52) U.S. Cl.
CPC ............ *C11D 3/38636* (2013.01); *C11D 1/22* (2013.01); *C11D 1/29* (2013.01); *C12Y 302/01006* (2013.01)

(58) Field of Classification Search
CPC .......................... C12N 9/24; C12Y 3002/01006
See application file for complete search history.

(56) References Cited

U.S. PATENT DOCUMENTS

| 5,871,966 | A | 2/1999 | Kofod |
|---|---|---|---|
| 6,140,096 | A * | 10/2000 | Kofod .................... A21D 8/042 435/200 |
| 6,176,970 | B1 | 1/2001 | Staton |
| 6,317,419 | B1 | 11/2001 | Olafsson |
| 6,403,549 | B1 | 6/2002 | De Lima |
| 7,960,148 | B2 | 6/2011 | Steer |
| 7,986,959 | B2 | 7/2011 | Malladi |
| 10,988,715 | B2 | 4/2021 | Lant |
| 2009/0238811 | A1 | 9/2009 | Mcdaniel et al. |
| 2010/0189706 | A1 | 7/2010 | Chang |
| 2010/0210745 | A1 | 8/2010 | Mcdaniel et al. |
| 2010/0233146 | A1 | 9/2010 | Mcdaniel |
| 2011/0093970 | A1 | 4/2011 | Arioli |
| 2011/0240064 | A1 | 10/2011 | Wales et al. |
| 2011/0250626 | A1 | 10/2011 | Williams et al. |
| 2012/0097194 | A1 | 4/2012 | Mcdaniel et al. |
| 2014/0193889 | A1 | 7/2014 | Mcdaniel |
| 2014/0196631 | A1 | 7/2014 | Mcdaniel |
| 2015/0139977 | A1 | 5/2015 | Weiner |
| 2015/0191607 | A1 | 7/2015 | Mcdaniel |
| 2016/0319227 | A1 | 11/2016 | Lant |
| 2017/0130215 | A1 | 5/2017 | Steer |
| 2017/0347664 | A1 | 12/2017 | Thompson |
| 2020/0109297 | A1 | 4/2020 | Mcdaniel |
| 2020/0291332 | A1 | 9/2020 | Lant |
| 2020/0291333 | A1 | 9/2020 | Lant |

FOREIGN PATENT DOCUMENTS

| WO | 9206210 A1 | 4/1992 |
|---|---|---|
| WO | WO9206210 A1 | 4/1992 |
| WO | 9701629 A1 | 1/1997 |
| WO | 2018086008 A1 | 5/2018 |

OTHER PUBLICATIONS

U.S. Appl. No. 16/816,403, filed Mar. 12, 2020, Neil Joseph Lant.
U.S. Appl. No. 16/816,429, filed Mar. 12, 2020, Neil Joseph Lant.
EP Search Report for appl. No. 19162988.0-1120, dated 6-13-1, 10 pages.
EP Search Report for appl. No. 19162993.0-1120, dated Jun. 13, 2019, 12 pages.
"Glycoside Hydrolase Family 16 Enzymes", available at http://www.cazy.org/GH16.html, accessed Oct. 26, 2020, 2 pages.
All Office Actions; U.S. Appl. No. 16/816,403.
All Office Actions; U.S. Appl. No. 16/816,429.
Database UniProt Accession No. D3EJV4, retrieved from Internet http://ibis/exam/dbfetch.jsp?id=UNIPROT:D3EJV4, on Jun. 3, 2019, 1 page.
Database UniProt Accession No. I7DGV4, retrieved from Internet http://ibis/exam/dbfetch.jsp?id=UNIPROT:I7DGV4, on Jun. 4, 2019, 1 page.
International Search Report and Written Opinion; Application No. PCT/US2020/022335; dated May 14, 2020; 18 pages.
International Search Report and Written Opinion; Application No. PCT/US2020/022337; dated May 13, 2020; 19 pages.
International Search Report and Written Opinion; Application No. PCT/US2020/022383; dated May 13, 2020; 18 pages.
Labourel et al., Database UniProt, Accession No. G0L2L9, Oct. 2011, 19 pages.
Legentil et al., "Molecular Interactions of β-(1,3)-Glucans with Their Receptors", Molecules, vol. 20, 2015, pp. 9745-9766.

(Continued)

*Primary Examiner* — Tekchand Saidha
(74) *Attorney, Agent, or Firm* — Carrie Schwartz

(57) ABSTRACT

Cleaning compositions comprising endo-β-1,3-glucanase enzyme and cleaning adjunct. Methods of treating surfaces including fabrics by contacting the surface with an aqueous was liquor having the cleaning composition therein. The compositions and methods are particularly for cleaning cotton fabrics. The compositions and methods are particularly for removal of soils containing callose, curdlan, pachyman, scleroglucan or schizophyllan. The compositions and methods are particularly for improving whiteness of a fabric, improved soil removal from a fabric, for malodour removal from a fabric, for anti-wrinkle benefits and/or for improved drying of a fabric.

12 Claims, No Drawings

Specification includes a Sequence Listing.

(56) References Cited

OTHER PUBLICATIONS

Spilliaert et al., "Cloning and Sequencing of a Rhodothermus marinus Gene, bglA, Coding for a Thermostable β-Glucanase and its Expression in *Escherichia coli*", European Journal of Biochemistry, vol. 224, 1994, pp. 923-930.

\* cited by examiner

CLEANING COMPOSITIONS COMPRISING ENZYMES

REFERENCE TO A SEQUENCE LISTING

This application contains a Sequence Listing in computer readable form. The computer readable form is incorporated herein by reference.

FIELD OF THE INVENTION

The present invention relates to cleaning compositions and methods of cleaning comprising endo-β-1,3-glucanase enzyme. The compositions and methods of the invention are suitable for use in household cleaning or treatment compositions, in particular laundry and hard surface cleaners including dish washing compositions, including hand wash and automatic laundry and/or dish washing compositions. The invention is particularly useful for cleaning laundry. The present invention also relates to methods of making cleaning compositions.

BACKGROUND OF THE INVENTION

In cleaning applications degradation of whiteness and soil or stain removal are continuing problems. There are many cleaning technologies aimed at mitigating such problems however, it is a constant challenge to provide improved efficacy and especially in an environmentally favourable manner. In automatic washing machines, both for laundry and dishwashing, these problems are compounded by the increased use of low (e.g., cold water) wash temperatures and shorter washing cycles. In hard surface cleaners, for use both inside homes and outside homes, for example for car-washing and cleaning other outdoor areas, such as patio and decking there is an increased desire for environmentally sensitive cleaning compositions.

The present inventors have found that natural impurities contribute to whiteness degradation and may also adhere other soils which contact the surfaces during use or even during the washing process. Such natural impurities may also be present in soils contacting household items.

Thus, it is an object of the present invention to provide cleaning compositions which can be used in washing, dishwashing and/or cleaning processes, even at low temperatures, which will counteract whiteness degradation and/or remove soils containing natural impurities. It is known to incorporate glucanase enzymes into cleaning compositions, for example as described in WO2005/003319. Such glucanase enzymes hydrolyse glucoside bonds. There are many different glucanase enzymes, for example endo-beta-1,3(4)-glucanase enzymes which hydrolyse both 1,3 and 1,4 linkages in beta glucans as well as endo-beta-1,3:1,4-glucanase enzymes, endo-beta-1,4-glucanase enzymes and endo-beta-1,3-glucanase enzymes. The present inventors have found that certain endo-beta-1,3-glucanase enzymes are particularly useful for stain removal in cleaning compositions comprising surfactant. The invention is particularly useful for laundry detergent compositions.

SUMMARY OF THE INVENTION

The present invention provides a cleaning composition comprising: an endo-β-1,3-glucanase enzyme; and a cleaning adjunct, wherein the endo-β-1,3-glucanase enzyme has at least 60% or at least 70% identity to one or more of the amino acid sequences selected from: SEQ ID NO: 1, SEQ ID NO: 2, SEQ ID NO: 3, SEQ ID NO: 4, SEQ ID NO: 5, SEQ ID NO: 6 and SEQ ID NO: 7.

The endo-β-1,3-glucanase is preferably from E.C. class 3.2.1.39.

The endo-β-1,3-glucanase enzyme is preferably obtained from *Paenibacillus* sp, *Zobellia galactanivorans*, *Thermotoga petrophila* or *Trichoderma* sp micro-organism, preferably *Paenibacillus* sp or *Zobellia galactanivorans*, most preferably *Paenibacillus* sp.

The invention also provides a method of treating a surface, preferably a textile, comprising: (i) forming an aqueous wash liquor comprising water and the composition comprising endo-β-1,3-glucanase enzyme; and (ii) treating the surface with the aqueous wash liquor, preferably at a temperature of 60° C. or less, or more preferably at a temperature of 40° C. or 35° C. or less, most preferably at a temperature of 30° C. or less; and (iii) rinsing the surface. The compositions and methods herein are particularly useful for treating a surface comprising cotton, which may be in the form of fibres or fabric, for example cotton or a mixed cotton fabric, preferably polycotton.

The invention also relates to the use of a composition or method as described above for cleaning or removal of callose or a callose-containing stain; cleaning or removal of curdlan or a curdlan-containing stain; cleaning or removal of pachyman or a pachyman-containing stain; cleaning or removal of scleroglucan or a scleroglucan-containing stain; or cleaning or removal of schizophyllan or schizophyllan-containing stain.

The invention also relates to the use of a composition or method as described above for: improving whiteness of a fabric, preferably a cotton-containing fabric; improved soil removal from a fabric, preferably a cotton-containing fabric; malodour reduction or removal from a fabric, preferably a cotton-containing fabric; anti-wrinkle benefits on a fabric, preferably a cotton-containing fabric; improved drying of a fabric, preferably a cotton-containing fabric.

DETAILED DESCRIPTION OF THE INVENTION

Definitions

Parent or Parent endo-β-1,3-glucanase enzyme: The term "parent" or "parent endo-β-1,3-glucanase" means an endo-β-1,3-glucanase to which an alteration is made to produce the enzyme variants. The parent may be a naturally occurring (wild-type) polypeptide or a variant thereof. For example, the parent may be any of SEQ ID Nos: 1, 2, 3, 4, 5, 6 or 7 listed herein.

Sequence Identity: The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment−
Total Number of Gaps in Alignment)

Alternatively, the parameters used may be gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment−Total Number of Gaps in Alignment)

Variant: The term "variant" means a polypeptide having endo-β-1,3-glucanase activity comprising an alteration/mutation, i.e., a substitution, insertion, and/or deletion, at one or more (e.g. several) positions relative to the parent endo-β-1,3-glucanase. A substitution means a replacement of an amino acid occupying a position with a different amino acid; a deletion means removal of an amino acid occupying a position; and an insertion means adding 1-3 amino acids adjacent to and immediately following an amino acid occupying a position.

Wild-Type Enzyme: The term "wild-type" endo-β-1,3-glucanase means an endo-β-1,3-glucanase expressed by a naturally occurring microorganism, such as a bacterium, yeast, or filamentous fungus found in nature.

Endo-β-1,3-glucanase Enzyme

The endo-β-1,3-glucanase enzyme is an enzyme having activity for β-1,3 glucoside bonds in β-1,3-glucans and in addition preferably weak/no activity on β-1,3 glucoside bonds in mixed linkage glucans, having both 1,3- and 1,4-β-glucan bonds. Thus the endo-β-1,3-glucanase enzyme herein does not include endo-1,3-1,4-β-D glucan-4-glucanohydrolases (licheninases) (E.C. class 3.2.1.73) or endo-β-1,3 (4)-glucanase ((E.C. class 3.2.1.6). Preferably the endo-β-1,3-glucanase enzyme is from E.C. class 3.2.1.39. Endo-β-1,3-glucanase activity can be confirmed by activity to pachyman, curdlan, callose, schizophyllan and/or scleroglucan. Preferably the endo-β-1,3-glucanase enzyme herein will have activity on one or more of pachyman, carboxymethyl curdlan, callose, schizophyllan and/or scleroglucan greater than or equal to the activity demonstrated by the equivalent amount of active protein according to SEQ ID NO: 7 (30 degrees C., pH 8.0 or at the pH of the cleaning composition). Preferably the endo-β-1,3-glucanase enzyme herein will have activity on carboxymethyl curdlan for example P-CMCUR (available from Megazyme International, Bray, Ireland) greater than or equal to the activity demonstrated by the equivalent amount of active protein according to SEQ ID NO: 7 (30 degrees C., pH 8.0 or at the pH of the cleaning composition). Preferably the endo-β-1,3-glucanase enzyme herein will the same or less activity on barley β-glucan (for example P-BGBM from Megazyme International, Bray, Ireland) than that demonstrated by the equivalent amount of active protein according to SEQ ID NO: 7 (30 degrees C., pH 8.0 or the pH of the cleaning composition).

The endo-β-1,3-glucanase enzyme useful in the invention having endo-β-1,3-glucanase enzyme activity is preferably microbial in origin, preferably bacterial or fungal (for example Trichoderma sp), most preferably bacterial. Preferably the endo-β-1,3-glucanase enzyme is obtainable from Paenibacillus sp, Zobellia galactanivorans, Thermotoga petrophila micro-organism, preferably Paenibacillus sp or Zobellia galactanivorans, most preferably Paenibacillus sp. Preferably the endo-β-1,3-glucanase enzyme is from glycosyl hydrolase (GH) family 16 or 64, preferably GH family 16. Preferably the endo-β-1,3-glucanase enzyme has a carbohydrate binding module CBM 6 or CBM 56.

Preferably the endo-β-1,3-glucanase enzyme has at least 60%, or at least 70%, or at least 75%, or at least 80%, or at least 85%, or at least 90%, or at least 95%, or at least 96%, or at least 97%, or at least 98%, or at least 99%, or 100%, sequence identity to one or more of SEQ ID NO: 1, SEQ ID NO: 2, SEQ ID NO: 3, SEQ ID NO: 4, SEQ ID NO: 5, SEQ ID NO: 6 or SEQ ID NO: 7 listed herein. Thus, preferred endo-β-1,3-glucanase enzyme corresponds to the wild-type or is a variant of the wild-type of any one of SEQ ID NOs: 1, 2, 3, 4, 5, 6 or 7 listed herein.

When the endo-β-1,3-glucanase enzyme is a variant of a parent amino acid sequence, the parent endo-β-1,3-glucanase enzyme preferably has a sequence identity to the polypeptide of one or more of SEQ ID NOs: 1, 2, 3, 4, 5, 6 or 7 of at least 50% or at least 60%, or at least 70% or at least 80%, such as at least 85%, at least 90%, e.g. at least 92%, at least 93%, at least 94%, at least 95%, at least 96%, at least 97%, at least 98%, at least 99, or 100%, which has endo-β-1,3-glucanase enzyme activity. It may be preferred for the variant amino acid sequence to differ from the parent endo-β-1,3-glucanase by no more than ten amino acids, or no more than five amino acids, by four amino acids, by three amino acids, by two amino acids, and by one amino acid from the polypeptide of one or more of SEQ ID NOs: 1, 2, 3, 4, 5, 6 or 7.

The parent may be obtained from microorganisms of any genus. For purposes of the present invention, the term "obtained from" as used herein in connection with a given source shall mean that the parent encoded by a polynucleotide is produced by the source or by a cell in which the polynucleotide from the source has been inserted. In one aspect, the parent is secreted extracellularly. Variants may be prepared using any mutagenesis procedure known in the art, such as site-directed mutagenesis, synthetic gene construction, semi-synthetic gene construction, random mutagenesis, shuffling, etc.

The endo-β-1,3-glucanase enzyme may be incorporated into the cleaning compositions and methods of the invention in the form of a substantially pure enzyme. Alternatively, in particular where the enzyme is a variant of a wild-type enzyme, the variant is not recovered, but rather a host cell expressing the enzyme is used as the source of the endo-β-1,3-glucanase enzyme.

The endo-β-1,3-glucanase enzyme may be in the form of a liquid or a dry composition. For instance, the composition may be in the form of a granulate or a microgranulate. The endo-β-1,3-glucanase enzyme may be stabilized in accordance with methods known in the art.

The endo-β-1,3-glucanase enzyme is preferably present in the composition in an amount from 0.00005 to 5 wt % active protein, preferably from 0.0001 to 2 wt % active protein or from 0.0005 to 1 wt % active protein.

Surfactant

The present inventors have found that the enzyme provides good soil breakdown, however the removal of the products of the breakdown of the substrates and soils containing them is improved by the presence of surfactant. Therefore, preferably the cleaning composition comprises a surfactant. Preferably the weight ratio of surfactant to active endo-β-1,3-glucanase enzyme protein is at least 500:1, preferably at least 1000:1 or 1500:1 or 2000:1. The composition preferably comprises from 0.1 to 60 weight % or from 0.5 to 50 wt % or 1 to 40 wt % of the composition, surfactant. The surfactant preferably comprises a surfactant system comprising a mixture of more than one surfactants, which may be non-ionic including semi-polar and/or anionic and/or cationic and/or zwitterionic and/or ampholytic and/or amphoteric and/or semi-polar nonionic and/or mixtures thereof.

Preferably the composition comprises an anionic surfactant. Preferred anionic surfactants are sulfonate and sulfate surfactants, preferably alkylbenzene sulphonates and/or (optionally alkoxylated) alkyl sulfates. Particularly preferred anionic surfactant comprises linear alkylbenzenesulfonates (LAS). Preferred alkyl sulfates comprise alkyl ether sulfates, especially C-9-15 alcohol ether sulfates, especially those having an average degree of ethoxylation from 0.5 to 7, preferably from 1 to 5, C8-C16 ester sulfates and C10-C14 ester sulfates, such as mono dodecyl ester sulfates. In a preferred composition according to the invention the surfactant comprises anionic surfactant, preferably comprising alkyl benzene sulphonate and/or optionally ethoxylated alkyl sulfate, preferably having a degree of ethoxylation from 0 to 7, more preferably from 0.5 to 3. Isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ether sulfates (AES or AEOS or FES, also known as alcohol ethoxy sulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof are also suitable anionic surfactants. Preferably the cleaning composition comprises anionic surfactant, preferably comprising alkyl benzene sulphonate and/or optionally ethoxylated alkyl sulfate, preferably having a degree of ethoxylation from 0 to 7, more preferably from 0.5 to 3.

The anionic surfactants are preferably added to the detergent in the form of salts. Preferred cations are alkali metal ions, such as sodium and potassium. However, the salt form of the anionic surfactant may be formed in situ by neutralization of the acid form of the surfactant with alkali such as sodium hydroxide or an amine, such as mono-, di-, or tri-ethanolamine. Preferably the surfactant comprises non-ionic surfactant. The invention also provides a cleaning composition comprising: an endo-β-1,3-glucanase enzyme; and a surfactant wherein the surfactant comprises an anionic and a nonionic surfactant, preferably in a weight ratio of anionic to nonionic of from 30:1 to 1:2, preferably from 20:1 to 2:3 or 1:1.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Alcohol ethoxylates are particularly preferred, preferably having a C9-18 alkyl chain, preferably from C12-15 and preferably having an average degree of ethoxylation 3 to 9, more preferably from 3 to 7. Commercially available nonionic surfactants include Plurafac™, Lutensol™ and Pluronic™ from BASF, Dehypon™ series from Cognis and Genapol™ series from Clariant.

The cleaning composition preferably comprises from about 1% to about 60% by weight or preferably from 5 to 40% or 35% by weight of an anionic surfactant. The cleaning composition preferably comprises from 0.2% to about 40% of a non-ionic surfactant such as alcohol ethoxylate, nonyl-phenol ethoxylate, alkylpolyglycoside, alkyldimethylamine-oxide, ethoxylated fatty acid monoethanolamide, fatty acid monoethanolamide, polyhydroxy alkyl fatty acid amide, or N-acyl N-alkyl derivatives of glucosamine ("glucamides").

The weight ratio of surfactant to active endo-β-1,3-glucanase enzyme protein is preferably at least 500:1, preferably at least 1000:1 or at least 1500:1 or at least 2000:1, preferably being no greater than 500000:1, preferably no greater than 400000:1, or no greater than 200000:1 or up to 150000:1 or 100000:1, or 50000:1 or 10000:1.

Cleaning Compositions

The cleaning compositions of the present invention preferably relate to products for and/or methods relating to and/or use of the claimed compositions for air care, car care, dishwashing, fabric conditioning (including softening), laundry detergency, laundry and rinse additive and/or care, hard surface cleaning and/or treatment, and other cleaning for consumer or institutional use. According to the invention, the above endo-β-1,3-glucanase may typically be a component in a cleaning composition, such as a solid, liquid, gel and/or unit dose detergent composition, e.g., a laundry detergent composition or a dishwashing detergent composition. Especially preferred is a liquid laundry detergent composition.

The cleaning composition comprises a cleaning adjunct or mixture of cleaning adjuncts. One preferred cleaning adjunct as described above is a surfactant. Typically the cleaning adjunct will be present in the composition in an amount from 0.001 to 99.9 wt %, more typically from 0.01 to 80 wt % cleaning adjunct. Suitable cleaning adjuncts comprise: surfactants, builders, bleaches, bleach catalysts, colorants, bleach boosters, chelating agents, dye transfer agents, deposition aids, dispersants, additional enzymes, and enzyme stabilizers, catalytic materials, bleach activators, hydrogen peroxide, sources of hydrogen peroxide, optical brighteners, photoactivators, fluorescers, fabric hueing agents, fabric conditioners, preformed peracids, polymeric dispersing agents, clay soil removal/anti-redeposition agents, filler salts, hydrotropes, brighteners, suds suppressors, structure elasticizing agents, fabric softeners, hydrolyzable surfactants, preservatives, anti-oxidants, anti-shrinkage agents, germicides, fungicides, anti-tarnish, anti-corrosion agents, alkalinity sources, solubilizing agents, carriers, processing aids, pigments, dyes, perfumes and pH control agents, encapsulates, polymers. For example, these may include: bleach ingredients such as imine bleach boosters; sources of hydrogen peroxide such as percarbonate and/or perborate, especially percarbonate coated with material such as carbonate and/or sulphate salt, silicate salt, borosilicate, and any mixture thereof; pre-formed peracid, including pre-formed peracid in encapsulated form; transition metal catalysts; suds suppressors or suppressor systems such as silicone based suds suppressors and/or fatty acid based suds suppressors; fabric-softeners such as clay, silicone and/or quaternary ammonium compounds; flocculants such as polyethylene oxide; dye transfer inhibitors such as polyvinylpyrrolidone, poly 4-vinylpyridine N-oxide and/or copolymer of vinylpyrrolidone and vinylimidazole; fabric integrity components such as oligomers produced by the condensation of imidazole and epichlorhydrin; soil dispersants and soil anti-redeposition aids such as alkoxylated polyamines and ethoxylated ethyleneimine polymers; anti-redeposition components such as polyesters; carboxylate polymers such as maleic acid polymers or co-polymers of maleic and acrylic acid; perfumes such as perfume microcapsules, starch encapsulated accords, perfume spray-on; soap rings; aesthetic particles; dyes; fillers such as sodium sulphate and/or citrus fibres, although it may be preferred for the composition to be substantially free of fillers; silicate salt such as sodium silicate, including 1.6R and 2.0R sodium silicate, or sodium metasilicate; co-polyesters of di-carboxylic acids and diols; cellulosic polymers such as methyl cellulose, carboxymethyl cellulose, hydroxyethoxycellulose, or other alkyl or alkylalkoxy cellulose; solvents such as 1,2 propanediol, monoethanolamine; diethylene glycol, ethanol, and any mixture thereof; hydrotropes such as sodium cumene sulphonate, sodium xylene sulphonate, sodium toluene sulphonate, and any mixtures; organic acids such as citric acid; and any combination thereof. The composition may be such that the cleaning adjunct comprises one or more selected from the group consisting of (i) perfume microcapsule; (ii) fabric hueing agent; (iii) protease; (iv) amphiphilic cleaning polymer; (v) lipase, or (vi) mixtures thereof.

The cleaning composition preferably comprise one or more additional enzymes. Therefore a preferred composition comprises (a) endo-β-1,3-glucanase, and (b) one or more additional enzymes preferably selected from the group consisting of aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannanase, mannosidase, oxidase, pectinolytic enzyme, peptidoglutaminase, peroxidase, phytase, polyphenoloxidase, proteolytic enzyme, ribonuclease, transglutaminase, xylanase, xanthan lyase, xanthanase and mixtures thereof. Preferably the composition comprises additional enzymes selected from xanthan lyase, xanthanase, mannanase and mixtures thereof. Mannanase is particularly preferred. Xanthan lyase and xanthanase and mixtures thereof are also particularly preferred. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger*, or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola*, e.g., *Humicola insolens* or *Humicola lanuginosa;* or *Trichoderma*, e.g., *Trichoderma harzianum, Trichoderma koningii, Trichoderma longibrachiatum, Trichoderma reesei,* or *Trichoderma viride.*

Preferably the composition comprises a protease or mixtures of more than one protease, a lipase or mixtures of more than one lipase, a peroxidase or mixtures of more than one peroxidase, one or more amylolytic enzymes, e.g., an alpha-amylase, glucoamylase, maltogenic amylase, preferably an additional alpha amylase, one or mixtures of more than one CGTase and/or a cellulase or mixtures of more than one cellulase, mannanase (such as MANNAWAY™ from Novozymes, Denmark) or mixtures of more than one mannanase, pectinase, pectate lyase, cutinase, and/or laccase or mixtures of more than one of one or more of these.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts. Preferably, the product of the invention comprises at least 0.01 mg, preferably from about 0.05 to about 10, more preferably from about 0.1 to about 6, especially from about 0.2 to about 5 mg of active further enzyme/g of composition.

Proteases: Suitable proteases for use in combination with the variant proteases of the invention include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), especially those derived from *Bacillus*, such as *Bacillus* sp., *B. lentus, B. alkalophilus, B. subtilis, B. amyloliquefaciens, B. pumilus, B. gibsonii*, and *B. akibaii* described in WO2004067737, WO2015091989, WO2015091990, WO2015024739, WO2015143360, U.S. Pat. No. 6,312,936 B1, U.S. Pat. Nos. 5,679,630, 4,760,025, DE102006022216A1, DE102006022224A1, WO2015089447, WO2015089441, WO2016066756, WO2016066757, WO2016069557, WO2016069563, WO2016069569 and WO2016174234. Specifically, mutations S9R, A15T, V66A, A188P, V199I, Q239R, N255D (Savinase numbering system).

(b) subtilisins from *B. pumillus* such as the ones described in WO2019048486, WO2019048488, and WO2019048495 including variants comprising amino acid substitutions at positions 29, 48, 101, 130, 131, 133, 144, 224, 252, 271; and variants comprising a substitution at position 271 in combinations with one or more substitutions at the following positions; 18, 61, 92, 99, 137, 149, 156, 159, 162, 172, 192, 199, 217, 265.

(c) S8 proteases from *Bacillus* sp. NN018132, *Bacillus borgouniensis* and *Paenibacillus dendritiformis* such as the ones described in US20180340162.

(d) trypsin-type or chymotrypsin-type proteases, such as trypsin (e.g., of porcine or bovine origin), including the *Fusarium* protease described in WO 89/06270 and the chymotrypsin proteases derived from *Cellumonas* described in WO 05/052161 and WO 05/052146.

(e) metalloproteases, especially those derived from *Bacillus amyloliquefaciens* described in WO07/044993A2; from *Bacillus, Brevibacillus, Thermoactinomyces, Geobacillus, Paenibacillus, Lysinibacillus* or *Streptomyces* spp. Described in WO2014194032, WO2014194054 and WO2014194117; from *Kribella alluminosa* described in WO2015193488; and from *Streptomyces* and *Lysobacter* described in WO2016075078.

(f) protease having at least 90% identity to the subtilase from *Bacillus* sp. TY145, NCIMB 40339, described in WO92/17577 (Novozymes A/S), including the variants of this *Bacillus* sp TY145 subtilase described in WO2015024739, WO2015014790, WO2016066757 and US20190040376

(g) Halotolerant proteases such as the one described in WO2019105675.

Especially preferred additional proteases for the detergent of the invention are polypeptides demonstrating at least 90%, preferably at least 95%, more preferably at least 98%, even more preferably at least 99% and especially 100% identity with the wild-type enzyme from *Bacillus lentus*, comprising mutations at one or more, preferably two or more and more preferably three or more of the following positions, using the BPN' numbering system: 9, 15, 68, 76, 78, 87, 99, X101, 103, 104, 118, 118, 128, 129, 130, 167, 170, 194, 205, 206, 209, 222, 245. Most preferably the additional proteases for the detergent invention comprise one or more, preferably two or more and more preferably three or more of the following mutations using the BPN' numbering system and amino acid abbreviations as illustrated in WO00/37627 which is incorporated herein by reference: S9R, A15T, V68A, N76D, N87S, S99D, S99E, S99SD, S99A, S101G, S101M, S103A, V104N/I, G118V, G118R, S128L, P129Q, S130A, Y167A, R170S, A194P, V205I, Q206L/D/E, Y209W, M222S, and/or Q245R.

Most preferably the additional protease is selected from the group of proteases comprising the below mutations (BPN' numbering system) versus either the PB92 wild-type (SEQ ID NO:2 in WO 08/010925) or the subtilisin 309 wild-type (sequence as per PB92 backbone, except comprising a natural variation of N87S).

(i) G118V+S128L+P129Q+S130A
(ii) S101M+G118V+S128L+P129Q+S130A
(iii) N76D+N87R+G118R+S128L+P129Q+S130A+S188D+N248R
(iv) N76D+N87R+G118R+S128L+P129Q+S130A+S188D+V244R
(v) N76D+N87R+G118R+S128L+P129Q+S130A
(vi) V68A+N87S+S101G+V104N
(vii) S99AD
(viii) S99E
(ix) S9R+A15T+V68A+N218D+Q245R Suitable commercially available additional protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase®, Coronase®, Blaze®, Blaze Ultra® and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase®, Ultimase® and Purafect OXP® by Dupont; those sold under the tradename Opticlean® and Optimase® by Solvay Enzymes; and those available from Henkel/Kemira, namely BLAP (sequence shown in FIG. 29 of U.S. Pat. No. 5,352,604 with the following mutations S99D+S101 R+S103A+V104I+G159S, hereinafter referred to as BLAP), BLAP R (BLAP with S3T+V41+V199M+V205I+L217D), BLAP X (BLAP with S3T+V41+V205I) and BLAP F49 (BLAP with S3T+V41+A194P+V199M+V205I+L217D); and KAP (*Bacillus alkalophilus* subtilisin with mutations A230V+S256G+S259N) from Kao.

Especially preferred for use herein in combination with the variant protease of the invention are commercial proteases selected from the group consisting of Properase®, Blaze®, Ultimase®, Everlase®, Savinase®, Excellase®, Blaze Ultra®, BLAP and BLAP variants.

Preferred levels of protease in the product of the invention include from about 0.05 to about 10, more preferably from about 0.5 to about 7 and especially from about 1 to about 6 mg of active protease/g of composition.

Lipases: The composition preferably comprises a lipase. The presence of oils and/or grease can further increase the resiliency of stains comprising mannans and other polysaccharides. As such, the presence of lipase in the enzyme package can further improve the removal of such stains. Suitable lipases include those of bacterial or fungal or synthetic origin. Chemically modified or protein engineered mutants are included. Examples of useful lipases include lipases from *Humicola* (synonym *Thermomyces*), e.g., from *H. lanuginosa* (*T lanuginosus*) or from *H. insolens*, a *Pseudomonas* lipase, e.g., from *P. alcaligenes* or *P. pseudoalcaligenes, P. cepacia P. stutzeri, P. fluorescens, Pseudomonas* sp. strain SD 705, *P. wisconsinensis*, a *Bacillus* lipase, e.g., from *B. subtilis* (Dartois et al. (1993), Biochemica et Biophysica Acta, 1131, 253-360), *B. stearothermophilus* or *B. pumilus*.

The lipase may be a "first cycle lipase" such as those described in U.S. Pat. No. 6,939,702 B1 and US PA 2009/0217464. In one aspect, the lipase is a first-wash lipase, preferably a variant of the wild-type lipase from *Thermomyces lanuginosus* comprising T231R and N233R mutations. The wild-type sequence is the 269 amino acids (amino acids 23-291) of the Swissprot accession number Swiss-Prot 059952 (derived from *Thermomyces lanuginosus* (*Humicola lanuginosa*)). Preferred lipases include those sold under the tradenames Lipex®, Lipolex® and Lipoclean®.

Other suitable lipases include: Liprl 139, e.g. as described in WO2013/171241; TfuLip2, e.g. as described in WO2011/084412 and WO2013/033318; *Pseudomonas stutzeri* lipase, e.g. as described in WO2018228880; *Microbulbifer thermotolerans* lipase, e.g. as described in WO2018228881; *Sulfobacillus acidocaldarius* lipase, e.g. as described in EP3299457; L1P062 lipase e.g. as described in WO2018209026; PinLip lipase e.g. as described in WO2017036901 and *Absidia* sp. lipase e.g. as described in WO2017005798.

A suitable lipase is a variant of SEQ ID NO:5 comprising:
(a) substitution T231R
and
(b) substitution N233R or N233C and
(c) at least three further substitutions selected from E1C, D27R, N33Q, G38A, F51V, G91Q, D96E, K98L, K98I, D111A, G163K, H198S, E210Q, Y220F, D254S, I255A, and P256T;

where the positions correspond to the positions of SEQ ID NO:5 and wherein the lipase variant has at least 90% but less than 100% sequence identity to the polypeptide having the amino acid sequence of SEQ ID NO: 5 and wherein the variant has lipase activity.

One preferred lipase is a variant of SEQ ID NO: 5 comprising the following substitutions: T231R, N233R, D27R, G38A, D96E, D111A, G163K, D254S and P256T One preferred lipase is a variant of SEQ ID NO: 5 comprising the following substitutions: T231R, N233R, N33Q, G91Q, E210Q, I255A.

Suitable lipases are commercially available from Novozymes, for example as Lipex Evity 100L, Lipex Evity 200L (both liquid raw materials) and Lipex Evity 105T (a granulate). These lipases have different structures to the products Lipex 100L, Lipex 100T and Lipex Evity 100T which are outside the scope of the invention.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum*. disclosed in U.S. Pat. Nos. 4,435,307, 5,648,263, 5,691,178, 5,776,757 and 5,691,178.

In one aspect, preferred enzymes include microbial-derived endoglucanases exhibiting endo-beta-1,4-glucanase activity (E.C. 3.2.1.4), preferably selected from the group comprising:

(a) a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403B2, preferred substitutions comprise one or more positions corresponding to positions 292, 274, 266, 265, 255, 246, 237, 224 and 221 of the mature polypeptide of SEQ ID NO: 2, and the variant has cellulase activity;

(b) a glycosyl hydrolase having enzymatic activity towards both xyloglucan and amorphous cellulose substrates, wherein the glycosyl hydrolase is selected from GH families 5, 7, 12, 16, 44 or 74;

(c) a glycosyl hydrolase having a sequence of at least 90%, 94%, 97% and even 99% identity to the amino acid sequence SEQ ID NO:3 in WO09/148983;

(d) Variants exhibiting at least 70% identity with SEQ ID NO: 5 in WO2017106676. Preferred substitutions comprise one or more positions corresponding to positions 4, 20, 23, 29, 32, 36, 44, 51, 77, 80, 87, 90, 97, 98, 99, 102, 112, 116, 135, 136, 142, 153, 154, 157, 161, 163, 192, 194, 204, 208, 210, 212, 216, 217, 221, 222, 225, 227, and 232;

(e) and mixtures thereof.

Suitable endoglucanases are sold under the tradenames Celluclean® and Whitezyme® (Novozymes A/S, Bagsvaerd, Denmark). Examples include Celluclean® 5000L, Celluclean® Classic 400L, Celluclean® Classic 700T, Celluclean® 4500T, Whitezyme® 1.5T, Whitezyme® 2.0L.

Other commercially available cellulases include Celluzyme®, Carezyme®, Carezyme® Premium (Novozymes A/S), Clazinase®, Puradax HA®, Revitalenz® 1000, Revitalenz® 2000 (Genencor International Inc.), KAC-500(B)® (Kao Corporation), Biotouch® FCL, Biotouch® DCL, Biotouch® DCC, Biotouch® NCD, Biotouch® FCC, Biotouch® FLX1 (AB Enzymes)

Amylases: Preferably the composition of the invention comprise an amylase. Suitable alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCBI 12289, NCBI 12512, NCBI 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) variants described in U.S. Pat. No. 5,856,164 and WO99/23211, WO 96/23873, WO00/60060, WO06/002643 and WO2017/192657, especially the variants with one or more substitutions in the following positions versus the AA560 enzyme listed as SEQ ID No. 12 in WO 06/002643: 26, 30, 33, 82, 37, 106, 118, 128, 133, 149, 150, 160, 178, 182, 186, 193, 202, 214, 231, 246, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(b) variants exhibiting at least 85%, preferably 90% identity with SEQ ID No. 4 in WO06/002643, the wild-type enzyme from *Bacillus* SP722, especially variants with deletions in the 183 and 184 positions and variants described in WO 00/60060, WO2011/100410 and WO2013/003659, particularly those with one or more substitutions at the following positions versus SEQ ID No. 4 in WO06/002643 which are incorporated herein by reference: 51, 52, 54, 109, 304, 140, 189, 134, 195, 206, 243, 260, 262, 284, 347, 439, 469, 476 and 477.

(c) variants exhibiting at least 90% identity with the wild-type enzyme from *Bacillus* sp.707 (SEQ ID NO:7 in U.S. Pat. No. 6,093,562), especially those comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations. Additional relevant mutations/deletions based on SP707 backbone include W48, A51, V103, V104, A113, R118, N125, V131, T132, E134, T136, E138, R142, S154, V165, R182, G182, H183, E190, D192, T193, I206, M208, D209, E212, V213, V214, N214, L217, R218, N219, V222, T225, T227, G229, I235, K242, Y243, S244, F245, T246, I250, S255, A256, H286, V291, T316, V317, V318, N417, T418, A419, H420, P421, I428, M429, F440, R443, N444, K445, Q448, S451, A465, N470, S472.

(d) variants described in WO 09/149130, preferably those exhibiting at least 90% identity with SEQ ID NO: 1 or SEQ ID NO:2 in WO 09/149130, the wild-type enzyme from *Geobacillus Stearophermophilus* or a truncated version thereof.

(e) variants described in WO10/115021, especially those exhibiting at least 75%, or at least 85% or at least 90% or at least 95% with SEQ ID NO:2 in WO10/115021, the alpha-amylase derived from *Bacillus* sp. TS-23.

(f) variants exhibiting at least 89% identity with SEQ ID NO:1 in WO2016091688, especially those comprising deletions at positions H183+G184 and additionally one or more mutations at positions 405, 421, 422 and/or 428.

(g) variants described in WO2014099523, especially those exhibiting at least 60% amino acid sequence identity with the "PcuAmyl α-amylase" from *Paenibacillus curdlanolyticus* YK9 (SEQ ID NO:3 in WO2014099523).

(h) variants described in WO2014099523, especially those exhibiting at least 60% amino acid sequence identity with the "CspAmy2 amylase" from *Cytophaga* sp. (SEQ ID NO:1 & 6 in WO2014164777. Especially those comprising one of more of the following deletions and/or mutations based on SEQ ID NO:1 in WO2014164777: R178*, G179*, T38N, N88H, N126Y, T129I, N134M, F153W, L171R, T180D, E187P, I203Y, G476K, G477E, Y303D.

(i) variants exhibiting at least 85% identity with AmyE from *Bacillus subtilis* (SEQ ID NO:1 in WO2009149271).

(j) variants exhibiting at least 90% identity with the wild-type amylase from *Bacillus* sp. KSM-K38 with accession number AB051102.

(k) variants described in WO2016180748, especially those exhibiting at least 80% identity with the mature amino acid sequence of AAI10 from *Bacillus* sp in SEQ ID NO: 7 in WO2016180748; those exhibiting at least 80% identity with the mature amino acid sequence of *Alicyclobacillus* sp. amylase in SEQ ID NO: 8 in WO2016180748, and those exhibiting at least 80% identity with the mature amino acid sequence of SEQ ID NO: 13 in WO2016180748, especially those comprising one or more of the following mutations H*, N54S, V56T, K72R, G109A, F113Q, R116Q, W167F, Q172G, A174S, G184T, N195F, V206L, K391A, P473R, G476K.

(l) variants described in WO2018060216, especially those exhibiting at least 70% identity with the mature amino acid sequence of SEQ ID NO: 4 in WO2018060216, the fusion molecule of *Bacillus amyloliquefaciens* and *Bacillus licheniformis*. Especially those comprising one or more substitutions at positions H1, NM, V56, K72, G109, F113, R116, T134, W140, W159, W167, Q169, Q172, L173, A174, R181, G182, D183, G184, W189, E194, N195, V206, G255, N260, F262, A265, W284, F289, 5304, G305, W347, K391, Q395, W439, W469, R444, F473, G476, and G477.

Preferably the amylase is an engineered enzyme, wherein one or more of the amino acids prone to bleach oxidation have been substituted by an amino acid less prone to oxidation. In particular it is preferred that methionine residues are substituted with any other amino acid. In particular it is preferred that the methionine most prone to oxidation is substituted. Preferably the methionine in a position equivalent to 202 in SEQ ID NO:11 is substituted. Preferably, the methionine at this position is substituted with threonine or leucine, preferably leucine.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL®, ATLANTIC®, ACHIEVE ALPHA®, AMPLIFY® PRIME, INTENSA® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE®, PREFERENZ S® series (including PREFERENZ S1000® and PREFERENZ S2000® and PURASTAR OXAM® (DuPont., Palo Alto, Calif.) and KAM® (Kao, 14-10 Nihonbashi Kayabacho, 1-chome, Chuo-ku Tokyo 103-8210, Japan).

Preferably, the product of the invention comprises at least 0.01 mg, preferably from about 0.05 to about 10, more preferably from about 0.1 to about 6, especially from about 0.2 to about 5 mg of active amylase/g of composition.

Preferably, the protease and/or amylase of the composition of the invention are in the form of granulates, the granulates comprise more than 29% of sodium sulfate by weight of the granulate and/or the sodium sulfate and the active enzyme (protease and/or amylase) are in a weight ratio of between 3:1 and 100:1 or preferably between 4:1 and 30:1 or more preferably between 5:1 and 20:1.

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME® (Novozymes A/S).

Pectate lyase: suitable pectate lyases include those sold under the tradenames Pectawash®, Pectaway®, X-Pect®, (all Novozymes A/S, Bagsvaerd, Denmark) Preferenz® F1000 (DuPont Industrial Biosciences).

Mannanases. Preferably the composition comprises a mannanase. As used herein, the term "mannanase" or "galactomannanase" denotes a mannanase enzyme defined according to that known in the art as mannan endo-1,4-beta-mannosidase and having the alternative names beta-mannanase and endo-1,4-mannanase and catalysing hydrolysis of 1,4-beta-D-mannosidic linkages in mannans, galactomannans, glucomannans, and galactoglucomannans Mannanases are classified according to the Enzyme Nomenclature as EC 3.2.1.78. Commercially available mannanases include those sold under the tradenames Mannaway® (Novozymes A/S, Bagsvaerd, Denmark), Effectenz® M1000, Mannastar® 375, Preferenz M100 and Purabrite® (all DuPont Industrial Biosciences, Palo Alto, Calif.). Preferred mannanases include: those having at least 85% sequence identity to residues 27-331 of SEQ ID NO: 8. SEQ ID NO: 8 corresponds to the full-length amino acid sequence of the Man7 mannanase endogenous to *Bacillus hemicellulosilyticus* including a signal sequence. Particularly preferred mannanases have at least 90% sequence identity to residues 27-331 of SEQ ID NO: 3, optionally comprising at least one substitution at positions 123, 158, 180, 272, 285, or 307 or a combination thereof; and mannanase from the the glycoside hydrolase family 26 that catalyze the hydrolysis of 1,4-3-D-mannosidic linkages in mannans, galactomannans and glucomannans. Suitable examples are described in WO2015040159.

Xanthan-degrading enzymes: Preferably the composition comprises a xanthan-degrading enzyme. Suitable enzymes for degradation of xanthan soils such as xanthan gum include combinations of xanthan endoglucanase and xanthan lyase. As used herein, the term xanthan endoglucanase denotes an enzyme exhibiting endo-beta-1,4-glucanase activity that is capable of catalysing hydrolysis of the 1,4-linked β-D-glucose polymeric backbone of xanthan gum in conjunction with a suitable xanthan lyase enzyme. Preferred xanthan endoglucanases have endo-beta-1,4-glucanase activity and a polypeptide having at least 60% identity to SEQ ID NO: 9. SEQ ID NO: 9 corresponds to the amino acid sequence of a xanthan endoglucanase endogenous to *Paenibacillus* sp-62047. The xanthan endoglucanase may be a variant with at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 9. The xanthan endoglucanase may have substitutions at one or more of positions 17, 20, 51, 53, 55, 56, 60, 63, 79, 87, 186, 192, 302, 311, 313, 387, 388, 390, 403, 408, 410, 416, 448, 451, 471, 472, 476, 489, 507, 512, 515, 538, 598, 599, 602, 605, 609, 676, 688, 690, 694, 697, 698, 699, 711, 719, 754, 756, 760, 781, 786, 797, 833, 834, 835 and 1048 of SEQ ID NO: 9. The xanthan endoglucanase may have substitutions at one or more of positions S17A, F20P, F20N, F20G, F20Y, K51Q, K51H, E53P, E53G, Y55M, V56M, Y60F, S63F, T87R, A186P, K192N, I320D, I302H, I302V, I302M, H311N, 5313D, I387T, K388R, K390Q, I403Y, E408D, E408S, E408P, E408A, E408G, E408N, P410G, Q416S, Q416D, A448E, A448W, A448S, K451S, G471S, S472Y, D476R, Q489P, K507R, K512P, S515V, S538C, Y579W, S598Q, A599S, I602T, I602D, V603P, 5605T, G609E, D676H, A688G, Y690F, T694A, T697G, R698W, T699A, T711V, T711Y, W719R, K754R, V756H, V756Y, S760G, T781M, N786K, T797S, A824D, N833D, Q834E, S835D and F1048W. As used herein, the term "xanthan lyase" denotes an enzyme that cleaves the β-D-mannosyl-β-D-1,4-glucuronosyl bond of xanthan and have been described in the literature. Xanthan lyases are classified according to the Enzyme Nomenclature as EC 4.2.2.12, and are known to be produced by many xanthan-degrading bacteria including *Bacillus, Corynebacterium* and *Paenibacillus* species. The xanthan lyase in accordance with the invention has xanthan lyase activity and comprises a polypeptide having at least 60% identity to SEQ ID NO: 10. SEQ ID NO: 10 corresponds to the amino acid sequence of a xanthan lyase endogenous to a *Paenibacillus* sp. The xanthan lyase may be a variant with at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 10. The xanthan lyase may be a variant with alterations at one or more positions selected from the group consisting of positions: 9, 15, 46, 58, 66, 89, 95, 100, 106, 109, 183, 188, 190, 203, 204, 221, 229, 234, 238, 240, 242, 243, 257, 258, 291, 293, 316, 320, 324, 329, 333, 339, 341, 352, 354, 360, 377, 399, 400, 419, 440, 450, 451, 454, 458, 481, 492, 567, 568, 578, 579, 582, 664, 672, 703, 728, 843, 855, 887, 892, 1008 and 1016 of SEQ ID NO: 10. The xanthan lyase may be a variant with alterations at one or more positions selected from the group consisting of positions 624, 631, 635, 649, 656, 752, 752, 754, 757, 769, 775, 777, 800, 801, 875, 911, and 915 of SEQ ID NO: 10. The xanthan lyase may be a variant with one or more substitutions selected from the group consisting of: K9R, N15T, L46D, A58L, S66H, Q89Y, K95E, S100D, N106Y, Q109R, Q109D, Q109F, Q109K, Q109A, K183Q, K183R, V188I, A190Q, A203P, K204R, A221 P, E229N, E229S, I234V, I238W, I238L, I238M, I240W, N242S, G243V, Y257W, R258E, K291R, A293G, A293P, K316R, K320R, L324Q, K329R, K333R, L339M, I341P, V352I, S354P, K360G, K360R, F377Y, N399K, K400R, F419Y, N440K, D450P, K451E, K451 R, A454V, D458S, K481R, A492L, A492H, K567R, G568A, S578K, S578R, S579R, S579K, S582K, A624E, T631N, S635E, T649K, I656V, T664K, N672D, I703L, M728V, G738L, P752K, P752R, G753E, S754E, S754R, S757D, A769D, L775A, D777R, V800P, D801G, A843P, K855R, K875T, K887R, N892Y, N892W, N892F, A911V, T915A, N1008D and K1016T of SEQ ID NO: 10.

Preferably the composition comprises a nuclease such as a RNase or DNase or mixtures thereof. The nuclease enzyme is an enzyme capable of cleaving the phosphodiester bonds between the nucleotide sub-units of nucleic acids. The nuclease enzyme herein is preferably a deoxyribonuclease or ribonuclease enzyme or a functional fragment thereof. By functional fragment or part is meant the portion of the nuclease enzyme that catalyzes the cleavage of phosphodiester linkages in the DNA backbone and so is a region of said nuclease protein that retains catalytic activity. Thus it includes truncated, but functional versions, of the enzyme and/or variants and/or derivatives and/or homologues whose functionality is maintained.

Preferably the nuclease enzyme is a deoxyribonuclease, preferably selected from any of the classes E.C. 3.1.21.x, where x=1, 2, 3, 4, 5, 6, 7, 8 or 9, E.C. 3.1.22.y where y=1, 2, 4 or 5, E.C. 3.1.30.z where z=1 or 2, E.C. 3.1.31.1 and mixtures thereof.

DNase: Suitable DNases include wild-types and variants of DNases defined by SEQ ID NOS: 1, 2, 3, 4, 5, 6, 7, 8 and 9 in WO2017162836 (Novozymes), and variants of the *Bacillus cibi* DNase including those described in WO2018011277 (Novozymes), incorporated herein by reference. Preferred DNases are as claimed in co-pending European Patent Application No. EP18202967.

RNase: suitable RNases include wild-types and variants of DNases defined by SEQ ID NOS: 3, 6, 9, 12, 15, 57, 58, 59, 60, 61, 62, 63, 64, 65, 66, 67, 72 and 73 in WO2018178061 (Novozymes), incorporated herein by reference.

Galactanase: Preferably the composition comprises a galactanase, ie. an extracellular polymer-degrading enzyme that includes an endo-beta-1,6-galactanase enzyme. The term "endo-beta-1,6-galactanase" or "a polypeptide having endo-beta-1,6-galactanase activity" means a endo-beta-1,6-galactanase activity (EC 3.2.1.164) from the glycoside hydrolase family 30 that catalyzes the hydrolytic cleavage of 1,6-3-D-galactooligosaccharides with a degree of polymerization (DP) higher than 3, and their acidic derivatives with 4-O-methylglucosyluronate or glucosyluronate groups at the non-reducing terminals. For purposes of the present disclosure, endo-beta-1,6-galactanase activity is determined according to the procedure described in WO 2015185689 in Assay I. Suitable examples from class EC 3.2.1.164 are described in WO 2015185689, such as the mature polypeptide SEQ ID NO: 2.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Film-forming coating materials may be applied for example by fluid bed techniques. Liquid enzyme preparations may, for instance, be stabilized by adding a polyol such as propylene glycol, a sugar or sugar alcohol, lactic acid or boric acid according to established methods.

The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Direct, Basic, Reactive or hydrolysed Reactive, Solvent or Disperse dyes. Examples of suitable small molecule dyes include for example small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes such as those described in EP1794275 or EP1794276, or dyes as disclosed in U.S. Pat. No. 7,208,459 B2, and mixtures thereof. In another aspect, suitable small molecule dyes include small molecule dyes selected from the group consisting of Colour Index numbers Acid Violet 17, Acid Violet 50 or 51, Direct Blue 71, Direct Violet 51, Direct Blue 1, Acid Red 88, Acid Red 150, Acid Blue 29, Acid Blue 113 or mixtures thereof.

Preferred are polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in WO2011/98355, WO2011/47987, US2012/090102, WO2010/145887, WO2006/055787 and WO2010/142503.

Preferred polymeric dyes comprise alkoxylated, preferably ethoxylated azo or anthraquinone or triarylmethane dyes. Ethoxylated thiophene azo dyes are especially preferred, for example polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Preferred hueing dyes include the alkoxylated thiophene azo whitening agents found in US2008/0177090 which may be optionally anionic, such as those selected from Examples 1-42 in Table 5 of WO2011/011799. Other preferred dyes are disclosed in U.S. Pat. No. 8,138,222.

Suitable pigments include pigments selected from the group consisting of Ultramarine Blue (C.I. Pigment Blue 29), Ultramarine Violet (C.I. Pigment Violet 15) and mixtures thereof. Pigments and/or dyes may also be added to add colour for aesthetic reasons. Preferred are organic blue, violet and/or green pigments.

Builders—The cleaning composition may further contain builders, such as builders based on carbonate, bicarbonate or silicates which may be Zeolites, such as Zeolite A, Zeolite MAP (Maximum Aluminium type P). Zeolites, useable in laundry preferably has the formula $Na_{12}(AlO_2)_{12}(SiO_2)_{12} \cdot 27H_2O$ and the particle size is usually between 1-10 µm for zeolite A and 0.7-2 µm for zeolite MAP. Other builders are Sodium metasilicate ($Na_2SiO_3 \cdot nH_2O$ or $Na_2Si_2O_5 \cdot nH_2O$) strong alkaline and preferably used in dish wash. In preferred embodiments, the amount of a detergent builder may be above 5%, above 10%, above 20%, above 30%, above 40% or above 50%, and may be below 80%, 65%. In a dishwash detergent, the level of builder is typically 40-65%, particularly 50-65% or even 75-90%.

Encapsulates—The composition may comprise an encapsulate. In one aspect, an encapsulate comprising a core, a shell having an inner and outer surface, said shell encapsulating said core. In one aspect of said encapsulate, said core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

In one aspect of said encapsulate, said core may comprise perfume. Such encapsulates are perfume microcapsules.

In one aspect of said encapsulate, said shell may comprise melamine formaldehyde and/or cross linked melamine formaldehyde.

In a one aspect, suitable encapsulates may comprise a core material and a shell, said shell at least partially surrounding said core material, is disclosed. At least 75%, 85% or even 90% of said encapsulates may have a fracture strength of from about 0.2 MPa to about 10 MPa, from about 0.4 MPa to about 5 MPa, from about 0.6 MPa to about 3.5 MPa, or even from about 0.7 MPa to about 3 MPa; and a benefit agent leakage of from 0% to about 30%, from 0% to about 20%, or even from 0% to about 5%.

In one aspect, at least 75%, 85% or even 90% of said encapsulates may have a particle size of from about 1 microns to about 80 microns, about 5 microns to 60 microns, from about 10 microns to about 50 microns, or even from about 15 microns to about 40 microns.

In one aspect, at least 75%, 85% or even 90% of said encapsulates may have a particle wall thickness of from about 30 nm to about 250 nm, from about 80 nm to about 180 nm, or even from about 100 nm to about 160 nm.

In one aspect, said encapsulates' core material may comprise a material selected from the group consisting of a perfume raw material and/or optionally a material selected from the group consisting of vegetable oil, including neat and/or blended vegetable oils including caster oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil and mixtures thereof; aromatic solvents, including benzene, toluene and mixtures thereof; silicone oils; and mixtures thereof.

In one aspect, said encapsulates' wall material may comprise a suitable resin including the reaction product of an aldehyde and an amine, suitable aldehydes include, formaldehyde. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof.

In one aspect, suitable formaldehyde scavengers may be employed with the encapsulates, for example, in a capsule slurry and/or added to a consumer product before, during or after the encapsulates are added to such consumer product.

Suitable capsules can be purchased from Appleton Papers Inc. of Appleton, Wis. USA.

In addition, the materials for making the aforementioned encapsulates can be obtained from Solutia Inc. (St Louis, Mo. U.S.A.), Cytec Industries (West Paterson, N.J. U.S.A.), sigma-Aldrich (St. Louis, Mo. U.S.A.), CP Kelco Corp. of San Diego, Calif., USA; BASF AG of Ludwigshafen, Germany; Rhodia Corp. of Cranbury, N.J., USA; Hercules Corp. of Wilmington, Del., USA; Agrium Inc. of Calgary, Alberta, Canada, ISP of New Jersey U.S.A., Akzo Nobel of Chicago, Ill., USA; Stroever Shellac Bremen of Bremen, Germany; Dow Chemical Company of Midland, Mich., USA; Bayer AG of Leverkusen, Germany; Sigma-Aldrich Corp., St. Louis, Mo., USA.

In one aspect, the composition may comprise an enzyme stabilizer selected from the group consisting of (a) inorganic salts selected from the group consisting of calcium salts, magnesium salts and mixtures thereof; (b) carbohydrates selected from the group consisting of oligosaccharides, polysaccharides and mixtures thereof; (c) mass efficient reversible protease inhibitors selected from the group consisting of phenyl boronic acid and derivatives thereof; and (d) mixtures thereof.

In another embodiment, the composition comprises: (1) reversible protease inhibitors such as a boron containing compound; (2) 1-2 propane diol; (3) calcium formate and/or sodium formate; and (4) any combination thereof.

In one aspect, the composition may comprise a structurant selected from the group consisting of diglycerides and triglycerides, ethylene glycol distearate microcrystalline cellulose, cellulose-based materials, microfiber cellulose, biopolymers, xanthan gum, gellan gum, and mixtures thereof.

Polymers

The consumer product may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers and amphiphilic polymers.

Amphiphilic Cleaning Polymers

Preferably, the amphiphilic cleaning polymer is a compound having the following general structure: $bis((C_2H_5O)(C_2H_4O)n)(CH_3)—N^+—C_xH_{2x}—N^+—(CH_3)-bis((C_2H_5O)(C_2H_4O)n)$, wherein n=from 20 to 30, and x=from 3 to 8, or sulphated or sulphonated variants thereof.

Amphiphilic alkoxylated grease cleaning polymers of the present invention refer to any alkoxylated polymer having balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure. These may comprise alkoxylated polyalkylenimines, preferably having an inner polyethylene oxide block and an outer polypropylene oxide block.

The core structure may comprise a polyalkylenimine structure comprising, in condensed form, repeating units of formulae (I), (II), (III) and (IV):

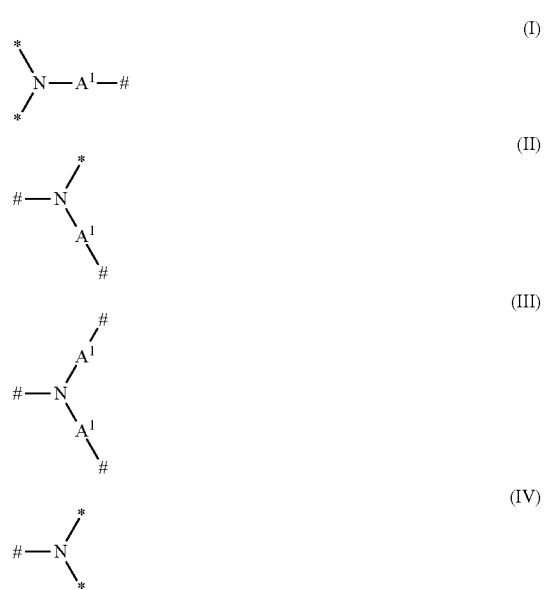

wherein # in each case denotes one-half of a bond between a nitrogen atom and the free binding position of a group $A^1$ of two adjacent repeating units of formulae (I), (II), (III) or (IV); * in each case denotes one-half of a bond to one of the alkoxylate groups; and $A^1$ is independently selected from linear or branched $C_2$-$C_6$-alkylene; wherein the polyalkylenimine structure consists of 1 repeating unit of formula (I), x repeating units of formula (II), y repeating units of formula (III) and y+1 repeating units of formula (IV), wherein x and y in each case have a value in the range of from 0 to about 150; where the average weight average molecular weight, Mw, of the polyalkylenimine core structure is a value in the range of from about 60 to about 10,000 g/mol.

The core structure may alternatively comprise a polyalkanolamine structure of the condensation products of at least one compound selected from N-(hydroxyalkyl)amines of formulae (I.a) and/or (I.b),

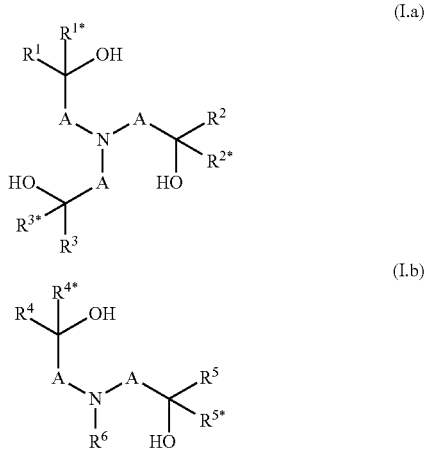

(I.a)

(I.b)

wherein A are independently selected from $C_1$-$C_6$-alkylene; $R^1$, $R^{1*}$, $R^2$, $R^{2*}$, $R^3$, $R^{3*}$, $R^4$, $R^{4*}$, $R^5$ and $R^{5*}$ are independently selected from hydrogen, alkyl, cycloalkyl or aryl, wherein the last three mentioned radicals may be optionally substituted; and $R^6$ is selected from hydrogen, alkyl, cycloalkyl or aryl, wherein the last three mentioned radicals may be optionally substituted.

The plurality of alkylenoxy groups attached to the core structure are independently selected from alkylenoxy units of the formula (V)

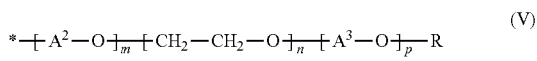

(V)

wherein * in each case denotes one-half of a bond to the nitrogen atom of the repeating unit of formula (I), (II) or (IV); $A^2$ is in each case independently selected from 1,2-propylene, 1,2-butylene and 1,2-isobutylene; $A^3$ is 1,2-propylene; R is in each case independently selected from hydrogen and $C_1$-$C_4$-alkyl; m has an average value in the range of from 0 to about 2; n has an average value in the range of from about 20 to about 50; and p has an average value in the range of from about 10 to about 50.

Specific embodiments of the amphiphilic alkoxylated grease cleaning polymers may be selected from alkoxylated polyalkylenimines having an inner polyethylene oxide block and an outer polypropylene oxide block, the degree of ethoxylation and the degree of propoxylation not going above or below specific limiting values. Specific embodiments of the alkoxylated polyalkylenimines according to the present invention have a minimum ratio of polyethylene blocks to polypropylene blocks (n/p) of about 0.6 and a maximum of about $1.5(x+2y+1)^{1/2}$. Alkoxykated polyalkyenimines having an n/p ratio of from about 0.8 to about $1.2(x+2y+1)^{1/2}$ have been found to have especially beneficial properties.

The alkoxylated polyalkylenimines according to the present invention have a backbone which consists of primary, secondary and tertiary amine nitrogen atoms which are attached to one another by alkylene radicals A and are randomly arranged. Primary amino moieties which start or terminate the main chain and the side chains of the polyalkylenimine backbone and whose remaining hydrogen atoms are subsequently replaced by alkylenoxy units are referred to as repeating units of formulae (I) or (IV), respectively. Secondary amino moieties whose remaining hydrogen atom is subsequently replaced by alkylenoxy units are referred to as repeating units of formula (II). Tertiary amino moieties which branch the main chain and the side chains are referred to as repeating units of formula (III).

Since cyclization can occur in the formation of the polyalkylenimine backbone, it is also possible for cyclic amino moieties to be present to a small extent in the backbone. Such polyalkylenimines containing cyclic amino moieties are of course alkoxylated in the same way as those consisting of the noncyclic primary and secondary amino moieties.

The polyalkylenimine backbone consisting of the nitrogen atoms and the groups $A^1$, has an average molecular weight Mw of from about 60 to about 10,000 g/mole, preferably from about 100 to about 8,000 g/mole and more preferably from about 500 to about 6,000 g/mole.

The sum (x+2y+1) corresponds to the total number of alkylenimine units present in one individual polyalkylenimine backbone and thus is directly related to the molecular weight of the polyalkylenimine backbone. The values given in the specification however relate to the number average of all polyalkylenimines present in the mixture. The sum (x+2y+2) corresponds to the total number amino groups present in one individual polyalkylenimine backbone.

The radicals $A^1$ connecting the amino nitrogen atoms may be identical or different, linear or branched $C_2$-$C_6$-alkylene radicals, such as 1,2-ethylene, 1,2-propylene, 1,2-butylene, 1,2-isobutylene, 1,2-pentanediyl, 1,2-hexanediyl or hexamethylen. A preferred branched alkylene is 1,2-propylene. Preferred linear alkylene are ethylene and hexamethylene. A more preferred alkylene is 1,2-ethylene.

The hydrogen atoms of the primary and secondary amino groups of the polyalkylenimine backbone are replaced by alkylenoxy units of the formula (V).

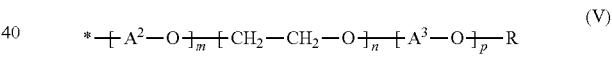

(V)

In this formula, the variables preferably have one of the meanings given below:

$A^2$ in each case is selected from 1,2-propylene, 1,2-butylene and 1,2-isobutylene; preferably $A^2$ is 1,2-propylene. $A^3$ is 1,2-propylene; R in each case is selected from hydrogen and $C_1$-$C_4$-alkyl, such as methyl, ethyl, n-propyl, isopropyl, n-butyl, isobutyl and tert.-butyl; preferably R is hydrogen. The index m in each case has a value of 0 to about 2; preferably m is 0 or approximately 1; more preferably m is 0. The index n has an average value in the range of from about 20 to about 50, preferably in the range of from about 22 to about 40, and more preferably in the range of from about 24 to about 30. The index p has an average value in the range of from about 10 to about 50, preferably in the range of from about 11 to about 40, and more preferably in the range of from about 12 to about 30.

Preferably the alkylenoxy unit of formula (V) is a non-random sequence of alkoxylate blocks. By non-random sequence it is meant that the $[-A^2-O-]_m$ is added first (i.e., closest to the bond to the nitrogen atom of the repeating unit of formula (I), (II), or (III)), the $[-CH_2-CH_2-O-]_n$ is added second, and the $[-A^3-O-]_p$ is added third. This orientation provides the alkoxylated polyalkylenimine with an inner polyethylene oxide block and an outer polypropylene oxide block.

The substantial part of these alkylenoxy units of formula (V) is formed by the ethylenoxy units —[CH$_2$—CH$_2$—O)]$_n$— and the propylenoxy units —[CH$_2$—CH$_2$(CH$_3$)—O]$_p$—. The alkylenoxy units may additionally also have a small proportion of propylenoxy or butylenoxy units —[A$^2$-O]$_m$—, i.e. the polyalkylenimine backbone saturated with hydrogen atoms may be reacted initially with small amounts of up to about 2 mol, especially from about 0.5 to about 1.5 mol, in particular from about 0.8 to about 1.2 mol, of propylene oxide or butylene oxide per mole of NH— moieties present, i.e. incipiently alkoxylated.

This initial modification of the polyalkylenimine backbone allows, if necessary, the viscosity of the reaction mixture in the alkoxylation to be lowered. However, the modification generally does not influence the performance properties of the alkoxylated polyalkylenimine and therefore does not constitute a preferred measure.

The amphiphilic alkoxylated grease cleaning polymers are present in the fabric and home care products, including but not limited to detergents, of the present invention at levels ranging from about 0.05% to 10% by weight of the fabric and home care product. Embodiments of the fabric and home care products may comprise from about 0.1% to about 5% by weight. More specifically, the embodiments may comprise from about 0.25 to about 2.5% of the grease cleaning polymer.

Carboxylate polymer—The consumer products of the present invention may also include one or more carboxylate polymers such as a maleate/acrylate random copolymer or polyacrylate homopolymer. In one aspect, the carboxylate polymer is a polyacrylate homopolymer having a molecular weight of from 4,000 Da to 9,000 Da, or from 6,000 Da to 9,000 Da.

Soil release polymer—The consumer products of the present invention may also include one or more soil release polymers having a structure as defined by one of the following structures (I), (II) or (III):

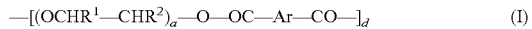
—[(OCHR$^1$—CHR$^2$)$_a$—O—OC—Ar—CO—]$_d$    (I)

—[(OCHR$^3$—CHR$^4$)$_b$—O—OC-sAr—CO—]$_e$    (II)

—[(OCHR$^5$—CHR$^6$)$_c$—OR$^7$]$_f$    (III)

wherein:
a, b and c are from 1 to 200;
d, e and f are from 1 to 50;
Ar is a 1,4-substituted phenylene;
sAr is 1,3-substituted phenylene substituted in position 5 with SO$_3$Me;
Me is Li, K, Mg/2, Ca/2, Al/3, ammonium, mono-, di-, tri-, or tetraalkylammonium wherein the alkyl groups are C$_1$-C$_{18}$ alkyl or C$_2$-C$_{10}$ hydroxyalkyl, or mixtures thereof;
R$^1$, R$^2$, R$^3$, R$^4$, R$^5$ and R$^6$ are independently selected from H or C$_1$-C$_{18}$ n- or iso-alkyl; and
R$^7$ is a linear or branched C$_1$-C$_{18}$ alkyl, or a linear or branched C$_2$-C$_{30}$ alkenyl, or a cycloalkyl group with 5 to 9 carbon atoms, or a C$_8$-C$_{30}$ aryl group, or a C$_6$-C$_{30}$ arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

Cellulosic polymer—The consumer products of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 Da to 300,000 Da.

The detergent may contain a bleaching system, which may comprise a H$_2$O$_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type. In general, when a bleaching agent is used, the compositions of the present invention may comprise from about 0.1% to about 50% or even from about 0.1% to about 25% bleaching agent by weight of the subject cleaning composition.

Chelating Agents—The consumer products herein may contain a chelating agent. Suitable chelating agents include copper, iron and/or manganese chelating agents and mixtures thereof. When a chelating agent is used, the subject consumer product may comprise from about 0.005% to about 15% or even from about 3.0% to about 10% chelating agent by weight of the subject consumer product. Suitable chelants (complexing agents) include DTPA (Diethylene triamine pentaacetic acid), HEDP (Hydroxyethane diphosphonic acid), DTPMP (Diethylene triamine penta(methylene phosphonic acid)), 1,2-Dihydroxybenzene-3,5-disulfonic acid disodium salt hydrate, ethylenediamine, diethylene triamine, ethylenediaminedisuccinic acid (EDDS), N-hydroxyethylethylenediaminetri-acetic acid (HEDTA), triethylenetetraaminehexaacetic acid (TTHA), N-hydroxyethyl-iminodiacetic acid (HEIDA), dihydroxyethylglycine (DHEG), ethylenediaminetetrapropionic acid (EDTP), methyl-glycine-diacetic acid (MGDA), glutamic-N,N-diacetic acid (GLDA), iminodisuccinic acid (IDS), carboxy methyl inulin; and salts derivatives thereof and mixtures thereof. Preferred chelants are selected from the group consisting of methyl-glycine-diacetic acid (MGDA), its salts and derivatives thereof, glutamic-N,N-diacetic acid (GLDA), its salts and derivatives thereof, iminodisuccinic acid (IDS), its salts and derivatives thereof, carboxy methyl inulin, its salts and derivatives thereof and mixtures thereof. Especially preferred complexing agent for use herein is selected from the group consisting of MGDA and salts thereof, especially preferred for use herein is the three-sodium salt of MGDA.

The enzymes used in the present invention may be stabilized using conventional stabilizing agents, and/or protease inhibitors e.g., a polyol such as propylene glycol or glycerol, a sugar or sugar alcohol, salts such as sodium chloride and potassium chloride, lactic acid, formic acid, boric acid, or a boric acid derivative, e.g., an aromatic borate ester, or a phenyl boronic acid derivative such as 4-form-ylphenyl boronic acid, or a peptide aldehyde such as di-, tri- or tetrapeptide aldehydes or aldehyde analogues (either of the form B1-B10-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO09118375, WO98/13459) or a protease inhibitor of the protein type such as RASI, BASI, WASI (bifunctional alpha-amylase/subtilisin inhibitors of rice, barley and wheat) or CI2 or SSI. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

The composition may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, organic solvents such as ethanol or perfumes. Furthermore, the detergent could contain a pre-spotter or a booster, which is added to the wash to increase the general cleaning level, some of these additives may also be used as a pre-treatment agent applied to the textile before the washing step.

It is at present contemplated that in the detergent composition any enzyme, in particular the enzyme essential to the present invention, may be added in an amount corresponding to 0.001-100 mg of enzyme protein per liter of wash liquor, preferably 0.005-5 mg of enzyme protein per liter of wash liquor, more preferably 0.01-1 mg of enzyme protein per liter of wash liquor and in particular 0.1-1 mg of enzyme protein per liter of wash liquor. However, the compositions of the present invention comprise at least 0.0001 to about 0.1% weight percent of pure enzyme protein, such as from about 0.0001% to about 0.01%, from about 0.001% to about 0.01% or from about 0.001% to about 0.01%. However, when using a formulated enzyme the detergent composition comprises from about 0.02% to about 20% weight percent, such as or from about 0.05% to about 15% weight, or from about 0.05 to about 20%, or from about 0.05% to about 5%, or from about 0.05% to about 3%.

The endo-β-1,3-glucanase enzyme useful in the present invention may additionally be incorporated in the detergent formulations disclosed in WO 97/07202, which is hereby incorporated as reference.

The detergent composition of the invention may be in any convenient form, e.g., a bar, a tablet, a powder, a granule, a paste, a gel, a liquid or a bead. The composition may be a powder-form all-purpose "heavy-duty" washing agent, a paste-form all-purpose, a heavy-duty liquid type, a liquid fine-fabric, a hand dishwashing agent, a light duty dishwashing agent, a high-foaming type. a machine dishwashing agent, a various tablet, a dishwash granular, a dish wash liquid, a rinse-aid type. The composition can also be in unit dose packages, including those known in the art and those that are water soluble, water insoluble and/or water permeable. A liquid detergent may be aqueous, typically containing up to 70% water and 0-30% organic solvent, or non-aqueous or a solution containing more than 0.5 g/L of the detergent composition.

The composition of the invention may for example be formulated as a hand or machine laundry detergent composition including a laundry additive composition suitable for pre-treatment of stained fabrics and a wash or rinse added fabric softener or freshener composition, or be formulated as a detergent composition for use in general household hard surface cleaning operations, or be formulated for hand or machine dishwashing operations. The detergent may be a powder, or granulated form, or it may be in the form of a liquid, gel or paste or in the form of a unit dose product such as a tablet or pouch, including multi-compartment pouches comprising liquids or solids of mixtures of liquids and solids in different compartments, or the detergent can be in the form of a sheet.

The present invention also provides use of a composition or method as described herein for reduction or removal of callose or a callose-containing stain. The present invention also provides use of a composition or method as described herein for removal of curdlan or a curdlan-containing stain. The present invention also provides use of a composition or method as described herein for removal of pachyman or a pachyman-containing stain. The present invention also provides use of a composition or method as described herein for removal of scleroglucan or a scleroglucan-containing stain. The present invention also provides use of a composition or method as described herein for removal of schizophyllan or schizophyllan-containing stain. The present invention also provides use of a composition or method as described herein for improving whiteness of a fabric, preferably a cotton-containing fabric. The present invention also provides use of a composition or method as described herein for improved soil removal from a fabric, preferably a cotton-containing fabric. The present invention also provides use of a composition or method as described herein for malodour removal from a fabric, preferably a cotton-containing fabric. As used herein "removal" can be partial or complete removal. The present invention also provides use of a composition or method as described herein for improved anti-wrinkle benefits on a fabric, preferably a cotton-containing fabric. The present invention also provides use of a composition or method as described herein for improved drying of a fabric, preferably a cotton-containing fabric.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Method of Use

The present invention includes a method for cleaning and/or treating a situs inter alia a surface or fabric. In one aspect, such method comprises the steps of optionally washing and/or rinsing said surface or fabric, contacting said surface or fabric with any consumer product disclosed in this specification then optionally washing and/or rinsing said surface or fabric is disclosed.

As used herein, washing includes but is not limited to contacting of the surface with the composition with scrubbing for example by rubbing the cleaning composition directly into the surface to be cleaned, and/or with mechanical agitation. It may be particularly preferred to use mechanical agitation to promote cleaning and removal of the broken-down soil by-products from the surface after the action of the endo-β-1,3-glucanase especially in aqueous wash liquor. This is particularly the case in the absence of surfactant or if low levels of surfactant are present. Drying of such surfaces or fabrics may be accomplished by any one of the common means employed either in domestic or industrial settings. Such means include but are not limited to forced air or still air drying at ambient or elevated temperatures at pressures between 5 and 0.01 atmospheres in the presence or absence of electromagnetic radiation, including sunlight, infrared, ultraviolet and microwave irradiation. In one aspect, said drying may be accomplished at temperatures above ambient by employing an iron wherein, for example, said fabric may be in direct contact with said iron for relatively short or even extended periods of time and wherein pressure may be exerted beyond that otherwise normally present due to gravitational force. In another aspect, said drying may be accomplished at temperatures above ambient by employing a dryer. Apparatus for drying fabric is well known and it is frequently referred to as a clothes dryer. In addition to clothes such appliances are used to dry many other items including towels, sheets, pillowcases, diapers and so forth and such equipment has been accepted as a standard convenience in many nations of the world substantially replacing the use of clothes lines for drying of fabric. Most dryers in use today use heated air which is passed over and or through the fabric as it is tumbled within the dryer. The air may be heated, for example, either electronically, via gas flame, or even with microwave radiation. Such air may be heated from about 15° C. to about 400° C., from about 25° C. to about 200° C., from about 35° C. to about 100° C., or even from about 40° C. to about 85° C. and used in the dryer to dry a surface and/or a fabric. As will be appreciated by one skilled in the art, the cleaning compositions of the present invention are ideally suited for use in laundry applications. Accordingly, the present invention includes a method for laundering a fabric. The method comprises the steps of contacting a fabric to be laundered with a said cleaning laundry solution comprising at least one embodiment of Applicants' cleaning composition, cleaning additive or mixture thereof. The fabric may comprise most any fabric capable of being laundered in normal consumer or institutional use conditions. The solution preferably has a pH of from about 8 to about 10.5. The compositions may be employed at concentrations of from about 500 ppm to about 15,000 ppm in solution. The water temperatures typically range from about 5° C. to about 90° C. The water to fabric ratio is typically from about 1:1 to about 30:1.

EXAMPLES

Example 1: Wash Performance of Liquid Detergent Composition Comprising an Endo-β-1,3-Glucanase The wash performance of an endo-β-1,3-glucanase on removal of cosmetic stains from cotton was determined in the context of a liquid laundry detergent as follows:

Stains were prepared on 5 cm×5 cm swatches of knitted cotton supplied by Warwick Equest Ltd, Consett, U.K. Makeup (Living Nature foundation, Pure Honey 30 ml, product code B0014596QE) was applied by sponge in four places on each swatch using a stencil with 1.2 cm diameter circular holes. The stained swatches were left to line dry for 24 hours before use, and image analysed before testing (see later).

Stain removal testing was conducted using a Tergotometer Detergent Tester, supplied by Copley Scientific Ltd, Nottingham, U.K. Two pots were filled with 400 mL tap water (6.5 grains per US gallon) heated to 40° C., and 1.04 mL Ariel liquid (purchased from Asda Stores Ltd in the UK in February 2019, product code Product Code: 6016650) added to each pot. Two stain swatches, each comprising four stains, were added to each pot, together with 5 cm×5 cm swatches of clean white knitted cotton ballast (Warwick Equest Ltd) to reach a total fabric load of 24 g.

The pots were then agitated, with addition of 0.4 mg active endo-β-1,3-glucanese enzyme (CZ0861, batch 18011, from NZYTech, Lisbon, Portugal) via a pipette to one of the two pots resulting in a wash concentration of 1 ppm active endo-β-1,3-glucanese. This enzyme is described by the supplier as belonging to Glycosyl Hydrolase family 16 and endogenous to *Paenibacillus* sp., and was confirmed by analysis to have a polypeptide sequence of greater than 98% identity to SEQ ID NO: 1. The temperature was maintained at 40° C. for the duration of the test. After 30 minutes, the wash water was drained, and the fabrics rinsed twice for 5 minutes in 400 mL cold tap water (6.5 grains per US gallon), before placing the washed stain swatches flat on a rack to dry under ambient conditions.

This process was repeated for three more times, with rotation of the treatments between the two pots. This resulted in a total of 32 washed stains per treatment, i.e. 4 external replicates, each comprising 2 swatches of 4 stains.

Pre- and post-analysis of stains was completed using Image Analysis (Illuminant D65/10) to calculate the difference in stain removal between the test and reference formulations.

Stain removal index (SRI) was calculated using the following equation, where $\Delta E_{AB}$ is the color difference between the stain-free region of the fabric before washing and the stain before washing, and $\Delta E_{AD}$ is the color difference between the stain-free region of the fabric before washing and the stain after washing.

$$SRI=100*(\Delta E_{AB}-\Delta E_{AD})/\Delta E_{AB},$$

Average test results are presented in the table below. They show that the addition of endo-β-1,3-glucanase leads to a large improvement in stain removal of 22.3 SRI units. This improvement is highly statistically significant, i.e. greater than 99.9% confidence level according to Student's T-test ($p<0.001$).

| Treatment | SRI (Stain Removal Index) | Standard Deviation |
|---|---|---|
| Ariel liquid without endo-β-1,3-glucanase | 48.3 | 3.9 |
| Ariel liquid plus 1 ppm wash concentration of active endo-β-1,3-glucanase (CZ08611) | 70.6 | 3.7 |

Example 2: Wash Performance of Liquid Detergent Composition Comparing Endo-β-Glucanase Enzymes The above procedure was repeated but using two stain swatches, each comprising five stains, image analysed for CIELab values (DigiEye, VeriVide, Leicester, U.K.) before testing. The tests were repeated using each of: 0.4 mg active endo-β-1,3-glucanese enzyme (CZ0861, batch 18011, from NZYTech, Lisbon, Portugal); 0.4 mg active endo-β-1,3(4)-glucanase (E-LICACT from *Clostridium thermocellum*, batch 160201b from Megazyme, Bray Co. Wicklow, Ireland); and 0.4 mg active endo-β-1,4-glucanase (Celluclean 5000L, batch CEN010785 from Novozymes A/S, Bagsvaerd, Denmark).

For each enzyme, the process was carried out four times, with rotation of the treatments between the two pots. This resulted in a total of 40 washed stains per treatment, i.e. 4 external replicates, each comprising 2 swatches of 5 stains. The washed stains were analysed for CIELab as before, and Stain Removal Index (SRI) calculated using the following equation:

$$SRI = \left(\frac{\Delta E_{pre\text{-}wash} - \Delta E_{post\text{-}wash}}{\Delta E_{pre\text{-}wash}}\right) \times 100$$

where $$\Delta E_{pre\text{-}wash} = \sqrt{[(L_{Clean} - L_{Stained})^2 + (a_{Clean} - a_{Stained})^2 + (b_{Clean} - b_{Stained})^2]}$$

and $$\Delta E_{post\text{-}wash} = \sqrt{[(L_{Clean} - L_{Washed})^2 + (a_{Clean} - a_{Washed})^2 + (b_{Clean} - b_{Washed})^2]}$$

| Treatment | SRI | CI (95%) |
|---|---|---|
| Nil | 57 | 3.4 |
| Endo-β-1,3-Glucanase | 74 | 2.0 |
| Endo-β-1,3(4)-Glucanase | 57 | 1.6 |
| Endo-β-1,4-Glucanase | 56 | 1.8 |

The results show that only the endo-β-1,3-glucanase in accordance with the invention significantly improves the removal of makeup stains from cotton, increasing removal from 57 to 74%. This improvement is highly significant and noticeable to the eye.

DETERGENT EXAMPLES

Examples 1-6. Granular Laundry Detergent Compositions Designed for Hand Washing or Top-Loading Washing Machines

|  | 1 (wt %) | 2 (wt %) | 3 (wt %) | 4 (wt %) | 5 (wt %) | 6 (wt %) |
|---|---|---|---|---|---|---|
| Linear alkylbenzenesulfonate | 20 | 22 | 20 | 15 | 20 | 20 |
| C12-14 Dimethylhydroxyethyl ammonium chloride | 0.7 | 0.2 | 1 | 0.6 | 0.0 | 0.0 |
| AE3S | 0.9 | 1 | 0.9 | 0.0 | 0.5 | 0.9 |
| AE7 | 0.0 | 0.0 | 0.0 | 1 | 0.0 | 3 |
| Sodium tripolyphosphate | 5 | 0.0 | 4 | 9 | 2 | 0.0 |
| Zeolite A | 0.0 | 1 | 0.0 | 1 | 4 | 1 |
| 1.6R Silicate (SiO2:Na2O at ratio 1.6:1) | 7 | 5 | 2 | 3 | 3 | 5 |
| Sodium carbonate | 25 | 20 | 25 | 17 | 18 | 19 |
| Polyacrylate MW 4500 | 1 | 0.6 | 1 | 1 | 1.5 | 1 |
| Random graft copolymer[1] | 0.1 | 0.2 | 0.0 | 0.0 | 0.0 | 0.0 |
| Carboxymethyl cellulose | 1 | 0.3 | 1 | 1 | 1 | 1 |
| Protease (Savinase ®, 32.89 mg active/g) | 0.1 | 0.1 | 0.1 | 0.1 |  | 0.1 |
| [5]DNase as defined herein (mg active per 100 g composition) | 4.0 | 6.0 | 10.0 | 2.2 | 4.4 | 1.5 |
| Lipase - Lipex ® (18 mg active/g) | 0.03 | 0.07 | 0.3 | 0.1 | 0.07 | 0.4 |
| [4]Amylase Stainzyme ® Plus (mg active) | 3.0 | 5.0 | 3.0 | 2.2 | 6.0 | 6.0 |
| [6]Endo-β-1,3-glucanase as defined herein (mg active per 100 g of detergent) | 12.0 | 15.0 | 3.2 | 4.3 | 9.2 | 17.0 |
| Fluorescent Brightener 1 | 0.06 | 0.0 | 0.06 | 0.18 | 0.06 | 0.06 |
| Fluorescent Brightener 2 | 0.1 | 0.06 | 0.1 | 0.0 | 0.1 | 0.1 |
| DTPA | 0.6 | 0.8 | 0.6 | 0.25 | 0.6 | 0.6 |
| MgSO4 | 1 | 1 | 1 | 0.5 | 1 | 1 |
| Sodium Percarbonate | 0.0 | 5.2 | 0.1 | 0.0 | 0.0 | 0.0 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Sulphonated zinc phthalocyanine | 0.0030 | 0.0 | 0.0012 | 0.0030 | 0.0021 | 0.0 |
| S-ACMC | 0.1 | 0.0 | 0.0 | 0.0 | 0.06 | 0.0 |
| Direct Violet 9 | 0.0 | 0.0 | 0.0003 | 0.0005 | 0.0003 | 0.0 |
| Acid Blue 29 | 0.0 | 0.0 | 0.0 | 0.0 | 0.0 | 0.0003 |
| Sulfate/Moisture | Balance | | | | | |

Examples 7-13. Granular Laundry Detergent Compositions Designed for Front-Loading Automatic Washing Machines

|  | 7 (wt %) | 8 (wt %) | 9 (wt %) | 10 (wt %) | 11 (wt %) | 12 (wt %) | 13 (wt %) |
|---|---|---|---|---|---|---|---|
| Linear alkylbenzenesulfonate | 8 | 7.1 | 7 | 6.5 | 7.5 | 7.5 | 11 |
| AE3S | 0 | 4.8 | 0 | 5.2 | 4 | 4 | 0 |

-continued

|  | 7 (wt %) | 8 (wt %) | 9 (wt %) | 10 (wt %) | 11 (wt %) | 12 (wt %) | 13 (wt %) |
| --- | --- | --- | --- | --- | --- | --- | --- |
| C12-14 Alkylsulfate | 1 | 0 | 1 | 0 | 0 | 0 | 1 |
| AE7 | 2.2 | 0 | 3.2 | 0 | 0 | 0 | 1 |
| C10-12 Dimethyl hydroxyethylammonium chloride | 0.75 | 0.94 | 0.98 | 0.98 | 0 | 0 | 0 |
| Crystalline layered silicate ($\delta$-Na2Si2O5) | 4.1 | 0 | 4.8 | 0 | 0 | 0 | 7 |
| Zeolite A | 5 | 0 | 5 | 0 | 2 | 2 | 4 |
| Citric Acid | 3 | 5 | 3 | 4 | 2.5 | 3 | 0.5 |
| Sodium Carbonate | 15 | 20 | 14 | 20 | 23 | 23 | 14 |
| Silicate 2R (SiO2:Na2O at ratio 2:1) | 0.08 | 0 | 0.11 | 0 | 0 | 0 | 0.01 |
| Soil release agent | 0.75 | 0.72 | 0.71 | 0.72 | 0 | 0 | 0.1 |
| Acrylic Acid/Maleic Acid Copolymer | 1.1 | 3.7 | 1.0 | 3.7 | 2.6 | 3.8 | 2 |
| Carboxymethylcellulose | 0.15 | 1.4 | 0.2 | 1.4 | 1 | 0.5 | 0.2 |
| Protease - Purafect ® (84 mg active/g) | 0.2 | 0.2 | 0.3 | 0.15 | 0.12 | 0.13 | 0.18 |
| Lipase - Lipex ® (18.00 mg active/g) | 0.05 | 0.15 | 0.1 | 0 | 0 | 0 | 0.1 |
| Cellulase - CellucleanTM (15.6 mg active/g) | 0 | 0 | 0 | 0 | 0.1 | 0.1 | 0 |
| [4]Amylase Stainzyme ® Plus (mg active) | 4.0 | 5.0 | 10 | 2.2 | 4.4 | 1.5 | 1.5 |
| Mannanase - Mannaway ® (4 mg active/g) | 0.05 | 0.1 | 0 | 0.05 | 0.1 | 0 | 0.1 |
| [5]DNase as defined herein (mg active per 100 g detergent) | 4.0 | 5.0 | 10.0 | 2.2 | 8.0 | 1.5 | 0.0 |
| [6]Endo-$\beta$-1,3-glucanase as defined herein (mg active per 100 g of detergent) | 3.3 | 9.2 | 12.0 | 4.7 | 3.7 | 13.2 | 3.3 |
| TAED | 3.6 | 4.0 | 3.6 | 4.0 | 2.2 | 1.4 | 1 |
| Percarbonate | 13 | 13.2 | 13 | 13.2 | 16 | 14 | 10 |
| Na salt of Ethylenediamine-N,N'-disuccinic acid, (S,S) isomer (EDDS) | 0.2 | 0.2 | 0.001 | 0.2 | 0.2 | 0.2 | 0.001 |
| Hydroxyethane di phosphonate (HEDP) | 0.2 | 0.2 | 0.5 | 0.2 | 0.2 | 0.2 | 0.5 |
| MgSO4 | 0.42 | 0.42 | 0.42 | 0.42 | 0.4 | 0.4 | 0 |
| Perfume | 0.5 | 0.6 | 0.5 | 0.6 | 0.6 | 0.6 | 0.8 |
| Suds suppressor agglomerate | 0.05 | 0.1 | 0.05 | 0.1 | 0.06 | 0.05 | 0.05 |
| Soap | 0.45 | 0.45 | 0.45 | 0.45 | 0 | 0 | 0 |
| Sulphonated zinc phthalocyanine (active) | 0.0007 | 0.0012 | 0.0007 | 0 | 0 | 0 | 0 |
| S-ACMC | 0.01 | 0.01 | 0 | 0.01 | 0 | 0 | 0 |
| Direct Violet 9 (active) | 0 | 0 | 0.0001 | 0.0001 | 0 | 0 | 0.001 |
| Sulfate/ Water & Miscellaneous |  |  |  | Balance |  |  |  |

*DNase is shown as mgs of active enzyme per 100 g of detergent.

Examples 14-21. Heavy Duty Liquid Laundry Detergent Compositions

|  | 14 (wt %) | 15 (wt %) | 16 (wt %) | 17 (wt %) | 18 (wt %) | 19 (wt %) | 20 (wt %) | 21 (wt %) |
| --- | --- | --- | --- | --- | --- | --- | --- | --- |
| C12-15 Alkylethoxy(1.8)sulfate | 14.7 | 11.6 | 0.0 | 16.3 | 0.0 | 17.3 | 20 | 12 |
| C11.8 Alkylbenzene sulfonate | 4.3 | 11.6 | 8.3 | 7.8 | 11.7 | 7.8 | 7 | 0 |
| C16-17 Branched alkyl sulfate | 1.7 | 1.29 | 0.0 | 3.09 | 0.0 | 3.3 | 0 | 0 |
| Cl2-14 Alkyl-9-ethoxylate | 0.9 | 1.07 | 0.0 | 1.31 | 0.0 | 1.31 | 5 | 0 |
| C12 dimethylamine oxide | 0.6 | 0.64 | 0.0 | 1.03 | 0.0 | 1.03 | 2 | 3 |
| Citric acid | 3.5 | 0.65 | 3 | 0.66 | 2.27 | 0.67 | 1 | 0 |
| Cl2-18 fatty acid | 1.5 | 2.32 | 3.6 | 1.52 | 0.82 | 1.52 | 1 | 0 |
| Sodium Borate (Borax) | 2.5 | 2.46 | 1.2 | 2.53 | 0.0 | 2.53 | 0 | 1 |
| Sodium C12-14 alkyl ethoxy 3 sulfate | 0.0 | 0.0 | 2.9 | 0.0 | 3.9 | 0.0 | 0 | 14 |
| C14-15 alkyl 7-ethoxylate | 0.0 | 0.0 | 4.2 | 0.0 | 1.9 | 0.0 | 0 | 4.2 |
| C12-14 Alkyl-7-ethoxylate | 0.0 | 0.0 | 1.7 | 0.0 | 0.5 | 0.0 | 0 | 1.7 |
| Ca chloride dihydrate | 0.0 | 0.0 | 0.0 | 0.0 | 0.045 | 0.0 | 0 | 0 |
| Ca formate | 0.09 | 0.09 | 0.0 | 0.09 | 0.0 | 0.09 | 0.09 | 0 |
| A compound: bis((C2H5O)(C2H4O)$n$)(CH3)—N+—C$x$H2$x$—N+—(CH3)-bis((C2H5O)(C2H4O)$n$); n is 20 to 30; x is 3 to 8, optionally sulphated or sulphonated | 0.0 | 0.0 | 1.2 | 0.0 | 0.66 | 0.0 | 0.0 | 1.2 |

|  | 14 (wt %) | 15 (wt %) | 16 (wt %) | 17 (wt %) | 18 (wt %) | 19 (wt %) | 20 (wt %) | 21 (wt %) |
| --- | --- | --- | --- | --- | --- | --- | --- | --- |
| Random graft co-polymer[1] | 0.0 | 1.46 | 0.5 | 0.0 | 0.83 | 0.0 | 0.0 | 0.5 |
| Ethoxylated Polyethylenimine [2] | 1.5 | 1.29 | 0.0 | 1.44 | 0.0 | 1.44 | 1.44 | 0.0 |
| Diethylene triamine pentaacetic acid | 0.34 | 0.64 | 0.0 | 0.34 | 0.0 | 0.34 | 0.34 | 0.0 |
| Diethylene triamine penta (methylene phosphonic acid) | 0.0 | 0.0 | 0.3 | 0.0 | 0.3 | 0.0 | 0.0 | 0.3 |
| 1-hydro xyethyidene-1,1-diphosphonic acid | 0.0 | 0.0 | 0.0 | 0.0 | 0.18 | 0.0 | 0.0 | 0.0 |
| Dihydroxybenzene-3,5-disulfonic acid disodium salt hydrate | 0.0 | 0.0 | 0.0 | 0.0 | 0.0 | 0.19 | 0.19 | 0.0 |
| Tinopal AMS-GX | 0.0 | 0.06 | 0.0 | 0.0 | 0.0 | 0.29 | 0.29 | 0.0 |
| Tinopal CBS-X | 0.2 | 0.17 | 0.0 | 0.29 | 0.0 | 0.0 | 0.0 | 0.0 |
| Tinopal TAS-X B36 | 0.0 | 0.0 | 0.0 | 0.0 | 0.091 | 0.0 | 0.0 | 0.0 |
| Amphiphilic alkoxylated grease cleaning polymer [3] | 1.28 | 1 | 0.4 | 1.93 | 0.0 | 1.93 | 1.93 | 0.4 |
| CHEC | 0.0 | 0.0 | 0.2 | 0.0 | 0.0 | 0.0 | 0.0 | 0.2 |
| Ethanol | 2 | 1.58 | 1.6 | 5.4 | 1.2 | 3.57 | 0 | 1.6 |
| Propylene Glycol | 3.9 | 3.59 | 1.3 | 4.3 | 0.0 | 3.8 | 3.8 | 1.3 |
| Diethylene glycol | 1.05 | 1.54 | 0.0 | 1.15 | 0.0 | 1.15 | 1.15 | 0.0 |
| Polyethylene glycol | 0.06 | 0.04 | 0.0 | 0.1 | 0.0 | 0.1 | 0.1 | 0.0 |
| [4]Amylase Amplify ® (mg active) | 8.0 | 7.0 | 2.5 | 4.0 | 3.0 | 1.7 | 3 | 2.5 |
| [5]DNase (mg active per 100 g detergent) | 7.0 | 3.0 | 2.5 | 4.0 | 1.25 | 10.0 | 3 | 2.5 |
| [6]Endo-β-1,3-glucanase as defined herein (mg active per 100 g of detergent) | 3.2 | 4.1 | 7.9 | 12.4 | 3.7 | 5.0 | 17.3 | 2.1 |
| Monoethanolamine | 3.05 | 2.41 | 0.4 | 1.26 | 0.31 | 1.13 | 1.13 | 0.4 |
| NaOH | 2.44 | 1.8 | 0.0 | 3.01 | 3.84 | 0.24 | 0.24 | 0.0 |
| Sodium Cumene Sulphonate | 0.0 | 0.0 | 1 | 0.0 | 0.95 | 0.0 | 0.0 | 1 |
| Sodium Formate | 0.0 | 0.11 | 0.0 | 0.09 | 0.2 | 0.12 | 0.12 | 0.0 |
| Polyethoxylated azo thiophene dye | 0.001 | 0.001 | 0.001 | 0.05 | 0.0001 | 0.0001 | 0.0001 | 0.001 |
| Water, Aesthetics (Dyes, perfumes) and Minors (Enzymes including lipase, protease, additional amylase each at 0.2% active protein, solvents, structurants) | balance | | | | | | | |

Examples 22-28. Unit Dose Laundry Detergent Compositions

Such unit dose formulations can comprise one or multiple compartments.

|  | 22 (wt %) | 23 (wt %) | 24 (wt %) | 25 (wt %) | 26 (wt %) | 27 (wt %) | 28 (wt %) |
| --- | --- | --- | --- | --- | --- | --- | --- |
| Alkylbenzene sulfonic acid | 14.5 | 14.5 | 14.5 | 14.5 | 14.5 | 23 | 23 |
| C12-18 alkyl ethoxy 2.5 sulfate | 7.5 | 7.5 | 7.5 | 7.5 | 7.5 | 16 | 16 |
| C12-18 alkyl 7-ethoxylate | 13.0 | 13.0 | 13.0 | 13.0 | 13.0 | 3.1 | 3.8 |
| C14-15 alkyl 9-ethoxylate | 0 | 0 | 0 | 0 | 0 | 1 | 0 |
| Citric Acid | 0.6 | 0.6 | 0.6 | 0.6 | 0.6 | 0.9 | 0.7 |
| Fatty Acid | 14.8 | 14.8 | 14.8 | 14.8 | 14.8 | 6.5 | 6 |
| Amylase (mg active) | 6 | 12 | 8 | 2 | 10 | 2 | 2 |
| Ethoxylated Polyethylenimine[2] | 4.0 | 4.0 | 4.0 | 4.0 | 4.0 | 4.0 | 4.0 |
| Protease (Purafect Prime ®, 40.6 mg active/g) | 1.4 | 2.0 | 0.9 | 1.2 | 0 | 1 | 1 |
| Cellulase (Celluclean, active protein) | 0.1 | 0.2 | 0.0 | 0.0 | 0.1 | 0 | 0 |
| [5]DNase described herein (mg active per 100 g detergent) | 3.0 | 2.0 | 1.0 | 4.0 | 2.0 | 1 | 1 |
| [4]Amylase Amplify ® (active protein) | 0.0 | 0.0 | 0.1 | 0.2 | 0.1 | 0.5 | 0.5 |
| [6]Endo-β-1,3-glucanase as defined herein (mg active per 100 g of detergent) | 2.2 | 3.1 | 2.3 | 5.2 | 5.3 | 12.2 | 5.4 |
| Hydroxyethane diphosphonic acid | 1.2 | 1.2 | 1.2 | 1.2 | 1.2 | 0 | 2.3 |
| Brightener | 0.3 | 0.3 | 0.3 | 0.3 | 0.3 | 0.2 | 0.2 |
| P-diol | 15.8 | 13.8 | 13.8 | 13.8 | 13.8 | 12.2 | 12.2 |

-continued

|  | 22 (wt %) | 23 (wt %) | 24 (wt %) | 25 (wt %) | 26 (wt %) | 27 (wt %) | 28 (wt %) |
|---|---|---|---|---|---|---|---|
| Glycerol | 6.1 | 6.1 | 6.1 | 6.1 | 6.1 | 4.0 | 3.8 |
| MEA | 8.0 | 8.0 | 8.0 | 8.0 | 8.0 | 8.6 | 10.2 |
| TIPA | 0.0 | 0.0 | 2.0 | 0.0 | 0.0 | 0.0 | 0.0 |
| TEA | 0.0 | 2.0 | 0.0 | 0.0 | 0.0 | 0.0 | 0.0 |
| Cumene sulphonate | 0.0 | 0.0 | 0.0 | 0.0 | 2.0 | 0.0 | 0.0 |
| Cyclohexyl dimethanol | 0.0 | 0.0 | 0.0 | 2.0 | 0.0 | 0.0 | 0.0 |
| Water | 10 | 10 | 10 | 10 | 10 | 10 | 10 |
| Structurant | 0.14 | 0.14 | 0.14 | 0.14 | 0.14 | 0.14 | 0.14 |
| Perfume | 1.9 | 1.9 | 1.9 | 1.9 | 1.9 | 1.9 | 1.9 |
| Buffers (monoethanolamine) | | | | To pH 8.0 | | | |
| Solvents (1,2 propanediol, ethanol) & minors | | | | To 100% | | | |

Example 29. Multiple Compartment Unit Dose Composition

Multiple compartment unit dose laundry detergent formulations of the present invention are provided below. In these examples the unit dose has three compartments, but similar compositions can be made with two, four or five compartments. The film used to encapsulate the compartments is polyvinyl alcohol.

| Base composition 1 | 24 (wt %) |
|---|---|
| Glycerol (min 99) | 5.3 |
| 1,2-propanediol | 10.0 |
| Citric Acid | 0.5 |
| Monoethanolamine | 10.0 |
| Caustic soda | — |
| Dequest 2010 | 1.1 |
| Potassium sulfite | 0.2 |
| $^5$DNase as defined herein (mg active) | 8.0 |
| $^6$Endo-β-1,3-glucanase as defined herein (mg active per 100 g of detergent) | 12.2 |
| Nonionic Marlipal C24EO7 | 20.1 |
| HLAS | 24.6 |
| Optical brightener FWA49 | 0.2 |
| C12-15 Fatty acid | 16.4 |
| Polymer Lutensit Z96 | 2.9 |
| Polyethyleneimine ethoxylate PEI600 E20 | 1.1 |
| MgCl2 | 0.2 |
| Solvents (1,2 propanediol, ethanol) | To 100% |

Multi-Compartment Formulations

| | Composition | | | | | |
|---|---|---|---|---|---|---|
| | 1 | | | 2 | | |
| | Compartment | | | | | |
| Active material | A | B | C | A | B | C |
| in Wt. % | Volume of each compartment | | | | | |
| | 40 ml | 5 ml | 5 ml | 40 ml | 5 ml | 5 ml |
| Perfume | 1.6 | 1.6 | 1.6 | 1.6 | 1.6 | 1.6 |
| Dyes | <0.01 | <0.01 | <0.01 | <0.01 | <0.01 | <0.01 |
| TiO2 | 0.1 | — | — | — | 0.1 | — |
| Sodium Sulfite | 0.4 | 0.4 | 0.4 | 0.3 | 0.3 | 0.3 |
| Acusol 305 | 1.2 | — | — | — | 2 | — |
| Hydrogenated castor oil | 0.14 | 0.14 | 0.14 | 0.14 | 0.14 | 0.14 |
| Base Composition 1 | Add to 100% | Add to 100% | Add to 100% | Add to 100% | Add to 100% | Add to 100% |

Example 30-33. Fabric Softener Compositions of the Present Invention

| | Weight % | | | |
|---|---|---|---|---|
| | Ex. 30 | Ex. 31 | Ex. 32 | Ex. 33 |
| NaHEDP | 0.007 | 0.007 | 0.007 | 0.007 |
| Formic acid | 0.044 | 0.044 | 0.044 | — |
| HCl | — | 0.009 | 0.009 | 0.009 |
| Preservative$^a$ | 0.022 | 0.01 | 0.01 | 0.01 |
| FSA$^b$ | 7.6 | 7.6 | 7.6 | 7.6 |
| Antifoam$^c$ | 0.1 | 0.1 | 0.1 | 0.1 |
| coconut oil | 0.3 | 0.3 | 0.3 | 0.3 |
| sopropanol | 0.78 | 0.78 | 0.77 | 0.77 |
| Encapsulated perfume$^d$ | 0.15 | 0.15 | 0.15 | 0.15 |
| dye | 0.015 | 0.015 | 0.015 | 0.015 |
| Cationic polymeric thickener$^e$ | 0.15 | 0.20 | 0.28 | 0.35 |
| $^5$DNase as defined herein (mg active per 100 g detergent) | 6.0 | 2.0 | 1.0 | 0.5 |
| $^6$Endo-β-1,3-glucanase as defined herein (mg active per 100 g of detergent) | 3.2 | 5.2 | 2.2 | 9.4 |
| 50:50 Blend of alkyl dimethyl benzyl ammonium chloride and alkyl dimethyl ethylbenzyl ammonium chloride$^f$ | — | — | 0.4 | — |
| Succinic acid | — | — | — | 5 |
| Perfume | 1.0 | 1.0 | 1.0 | 1.0 |
| deionized water | Balance | Balance | Balance | Balance |

Raw Materials and Notes for Composition Examples 1-33
Linear alkylbenzenesulfonate having an average aliphatic carbon chain length C11-C18
C12-18 Dimethylhydroxyethyl ammonium chloride
AE3S is C12-15 alkyl ethoxy (3) sulfate
AE7 is C12-15 alcohol ethoxylate, with an average degree of ethoxylation of 7
AE9 is C12-16 alcohol ethoxylate, with an average degree of ethoxylation of 9
HSAS is a mid-branched primary alkyl sulfate with carbon chain length of about 16-17 as disclosed in U.S. Pat. Nos. 6,020,303 and 6,060,443
Polyacrylate MW 4500 is supplied by BASF
Carboxymethyl cellulose is Finnfix® V supplied by CP Kelco, Arnhem, Netherlands
CHEC is a cationically modified hydroxyethyl cellulose polymer.
Phosphonate chelants are, for example, diethylenetetraamine pentaacetic acid (DTPA) Hydroxyethane di phosphonate (HEDP)
Savinase®, Natalase®, Stainzyme®, Lipex®, Celluclean™, Mannaway® and Whitezyme® are all products of Novozymes, Bagsvaerd, Denmark.

Purafect®, Purafect Prime® are products of Genencor International, Palo Alto, Calif., USA
Fluorescent Brightener 1 is Tinopal® AMS, Fluorescent Brightener 2 is Tinopal® CBS-X, Direct Violet 9 is Pergasol® Violet BN-Z NOBS is sodium nonanoyloxybenzenesulfonate
TAED is tetraacetylethylenediamine
S-ACMC is carboxymethylcellulose conjugated with C.I. Reactive Blue 19 product name AZO-CM-CELLULOSE
Soil release agent is Repel-o-Tex® PF
Acrylic Acid/Maleic Acid Copolymer is molecular weight 70,000 and acrylate:maleate ratio 70:30
EDDS is a sodium salt of ethylenediamine-N,N'-disuccinic acid, (S,S) isomer Suds suppressor agglomerate is supplied by Dow Corning, Midland, Mich., USA
HSAS is mid-branched alkyl sulfate
Liquitint® Violet CT polymeric hueing dye, supplied by Milliken, Spartanburg, S.C., USA
Polyethoxylated azo thiophene dye is Violet DD™ polymeric hueing dye, supplied by Milliken, Spartanburg, S.C., USA.
[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Polyethyleneimine (MW=600) with 20 ethoxylate groups per —NH.
[3] Amphiphilic alkoxylated polymer is a polyethylenimine (MW 600), prepared from a polymer that is derivatised to contain 24 ethoxylate groups per —NH and 16 Propoxylate groups per —NH.
[4] Amylase is shown as mgs of active enzyme per 100 g of detergent.
[5] DNase in all of these examples is shown as mgs of active enzyme per 100 g of detergent. DNase may comprise minor amounts of super oxide dismutase impurity.
[6] Endo-ß-1,3-glucanase in all of these examples is shown as mgs of active enzyme per 100 g of detergent
[a] Proxel GXL, 20% aqueous dipropylene glycol solution of 1,2-benzisothiazolin-3-one, supplied by Lonza.
[b] N,N-bis(hydroxyethyl)-N,N-dimethyl ammonium chloride fatty acid ester. The iodine value of the parent fatty acid of this material is between 18 and 22. The material as obtained from Evonik contains impurities in the form of free fatty acid, the monoester form of N,N-bis(hydroxyethyl)-N,N-dimethyl ammonium chloride fatty acid ester, and fatty acid esters of N,N-bis(hydroxyethyl)-N-methylamine
[c] MP10®, supplied by Dow Corning, 8% activity
[d] as described in U.S. Pat. No. 8,765,659, expressed as 100% encapsulated perfume oil
[e] Rheovis® CDE, cationic polymeric thickener supplied by BASF
[f] N,N-dimethyl octanamide and N,N-dimethyl decanamide in about a 55:45 weight ratio, tradename Steposol® M-8-10 from the Stepan Company The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

---

What is claimed is:

1. A cleaning composition comprising: (i) an endo-β-1,3-glucanase enzyme; and (ii) a surfactant, wherein the endo-β-1,3-glucanase enzyme has at least 95% sequence identity to SEQ ID NO: 1 or SEQ ID NO: 2 or SEQ ID NO: 3 or SEQ ID NO: 4 or SEQ ID NO: 5 or SEQ ID NO: 6 or SEQ ID NO: 7 and wherein the weight ratio of surfactant to active endo-β-1,3-glucanase enzyme protein is at least 500:1.

2. A cleaning composition according to claim 1 which is a laundry detergent composition.

3. A cleaning composition according to claim 1 wherein the endo-β-1,3-glucanase enzyme is of bacterial origin.

4. A cleaning composition according to claim 1 wherein the endo-β-1,3-glucanase enzyme is obtainable from *Paenibacillus* sp, *Zobellia galactanivorans, Thermotoga petrophila* micro-organism.

5. A cleaning composition according to claim 1 wherein the endo-β-1,3-glucanase enzyme is from glycosyl hydrolase (GH) family 16 or 64.

6. A cleaning composition according to claim 1 wherein the endo-β-1,3-glucanase enzyme has a carbohydrate binding module CBM 6 or CBM 56.

7. A cleaning composition according to claim 1 wherein the surfactant comprises an anionic surfactant.

8. A cleaning composition according to claim 1 wherein the surfactant comprises nonionic surfactant, in an amount from 1 to 30 wt % of the composition.

9. A cleaning composition according to claim 1 wherein the surfactant comprises an anionic and a nonionic surfactant in a weight ratio of anionic to nonionic of from 30:1 to 1:2.

10. A cleaning composition according to claim 7 wherein the anionic surfactant comprises alkyl benzene sulphonate, ethoxylated alkyl sulfate, or a combination thereof.

11. A cleaning composition according to claim 1 comprising an additional enzyme comprising mannanase, xanthan lyase, xanthanase, or a combination thereof.

12. A method of treating a surface, comprising: (i) forming an aqueous wash liquor comprising water and a composition according to claim 1; and (ii) treating the surface with the aqueous wash liquor at a temperature of from 5 to 40° C.; and (iii) rinsing the surface.

* * * * *

SEQUENCE LISTING

```
<160> NUMBER OF SEQ ID NOS: 10

<210> SEQ ID NO 1
<211> LENGTH: 763
<212> TYPE: PRT
<213> ORGANISM: Paenibacillus sp.

<400> SEQUENCE: 1

Met Lys Arg Ser Tyr Ala Thr Glu Arg Arg Tyr Leu Gln Lys Gly Leu
1               5                   10                  15

Ser Leu Phe Phe Ala Val Val Met Leu Ala Ser Val Gly Leu Trp Pro
                20                  25                  30

Ala Ser Lys Val Glu Ala Ala Asp Phe Thr Val Thr Ser Met Asp Tyr
            35                  40                  45

Phe Ser Ala Ala Asp Gly Pro Val Ile Ser Lys Ser Gly Val Gly Gln
        50                  55                  60

Ala Ser Tyr Gly Phe Val Met Pro Ile Phe Asn Gly Gly Ala Ala Thr
65                  70                  75                  80
```

-continued

```
Trp Asn Asp Val Ala Gln Asp Val Gly Val Lys Val Lys Val Gly Gly
                85                  90                  95
Ser Trp Val Asp Ile Asp Ser Val Ser Ser Phe Ile Tyr Asn Gln Asn
            100                 105                 110
Trp Gly His Trp Ser Asp Gly Gly Phe Thr Gly Tyr Trp Phe Thr Leu
        115                 120                 125
Ser Ala Thr Thr Glu Ile Gln Leu Tyr Ser Lys Ala Asn Gly Val Thr
    130                 135                 140
Leu Asp Tyr Arg Leu Val Phe Gln Asn Ile Asn Lys Thr Thr Ile Thr
145                 150                 155                 160
Ala Met Thr Pro Thr Gln Gly Pro Gln Ile Thr Ala Ser Phe Thr Gly
                165                 170                 175
Gly Ala Gly Phe Thr Tyr Pro Thr Phe Asn Asn Asp Pro Ala Val Thr
            180                 185                 190
Tyr Ala Ala Val Ala Asp Asp Leu Lys Val Phe Val Lys Pro Val Asn
        195                 200                 205
Ser Ser Thr Trp Ile Asp Ile Asp Asn Asn Ala Ala Ser Gly Trp Ile
    210                 215                 220
Tyr Asp His Asn Phe Gly Gln Phe Thr Asp Gly Gly Gly Tyr Trp
225                 230                 235                 240
Phe Asn Val Thr Glu Ser Ile His Val Lys Leu Glu Ser Lys Thr Ser
                245                 250                 255
Gly Val Asn Val Val Tyr Thr Ile Thr Phe Asn Glu Ala Val Arg Asn
            260                 265                 270
Ser Tyr Val Ile Thr Pro Tyr Glu Gly Thr Thr Phe Thr Ala Asp Ala
        275                 280                 285
Asn Gly Ser Ile Gly Ile Pro Leu Pro Lys Ile Asp Gly Gly Ala Pro
    290                 295                 300
Ile Gly Lys Glu Leu Asp Asn Phe Val Tyr Gln Ile Asn Ile Asn Gly
305                 310                 315                 320
Gln Trp Val Glu Leu Gly Asn Ser Gly Gln Ser Gly Phe Thr Tyr Ala
                325                 330                 335
Ala Asn Gly Tyr Asn Asn Met Ser Asp Ala Asn Gln Trp Gly Tyr Trp
            340                 345                 350
Ala Asp Tyr Ile Tyr Gly Leu Trp Phe Gln Pro Ile Gln Glu Asp Met
        355                 360                 365
Gln Ile Arg Ile Gly Tyr Pro Leu Asn Gly Gln Lys Gly Gly Ser Val
    370                 375                 380
Gly Ser Asn Tyr Val Asn Tyr Thr Leu Ile Gly Asn Pro Asp Ala Pro
385                 390                 395                 400
Arg Pro Asp Val Ser Asp Gln Glu Asp Ile Ala Ile Gly Thr Pro Ser
                405                 410                 415
Asp Pro Ala Ile Gln Gly Met Asn Leu Ile Trp Gln Asp Glu Phe Asn
            420                 425                 430
Gly Thr Thr Leu Asp Thr Ser Lys Trp Asn Tyr Glu Gln Gly Tyr Tyr
        435                 440                 445
Leu Asn Asp Asp Pro Asn Thr Trp Gly Trp Gly Asn Ala Glu Leu Gln
    450                 455                 460
His Tyr Thr Asp Ser Ala Gln Asn Val Phe Val Gln Asp Gly Lys Leu
465                 470                 475                 480
Asn Ile Arg Ala Leu Asn Asp Pro Lys Ser Phe Pro Gln Asp Pro Ser
                485                 490                 495
```

```
Arg Tyr Ala Gln Tyr Ser Ser Gly Lys Ile Asn Thr Lys Asn His Phe
                500                 505                 510

Thr Leu Lys Tyr Gly Arg Val Asp Phe Arg Ala Lys Leu Pro Thr Gly
            515                 520                 525

Asn Gly Val Trp Pro Ala Leu Trp Met Leu Pro Gln Asp Ser Pro Tyr
        530                 535                 540

Gly Thr Trp Ala Ala Ser Gly Glu Ile Asp Val Met Glu Ala Arg Gly
545                 550                 555                 560

Arg Leu Pro Gly Ser Thr Ser Gly Ala Val His Phe Gly Gly Thr Trp
                565                 570                 575

Pro Ala Asn Gln His Ile Ser Gly Glu Tyr His Phe Pro Glu Gly Gln
            580                 585                 590

Asn Ile Asn Asn Asp Tyr His Val Tyr Ser Val Val Trp Glu Glu Asp
        595                 600                 605

Asn Ile Lys Trp Tyr Val Asp Gly Lys Phe Phe Lys Val Thr Asn
610                 615                 620

Glu Gln Trp Tyr Ser Leu Ala Ala Pro Asn Asn Pro Asn Ala Pro Phe
625                 630                 635                 640

Asp Gln Pro Phe Tyr Leu Ile Met Asn Leu Ala Leu Gly Gly Asn Phe
                645                 650                 655

Asp Gly Gly Ile Ser Pro Asn Pro Ser Asp Ile Pro Val Thr Met Gln
            660                 665                 670

Val Asp Tyr Val Arg Val Tyr Lys Glu Asn Gly Ser Gly Asn Pro Gly
        675                 680                 685

Asn Val Pro Val Thr Gly Val Thr Leu Asn Pro Thr Ser Ala Gln Val
690                 695                 700

Glu Val Gly Gln Ser Leu Gln Leu Asn Ala Gly Ile Ala Pro Ser Asn
705                 710                 715                 720

Ala Thr Asn Lys Gln Val Thr Trp Ser Val Ser Gly Ala Ser Val Ala
                725                 730                 735

Ser Val Ser Gln Glu Gly Val Val Thr Gly Leu Ala Pro Gly Thr Ala
            740                 745                 750

Thr Val Thr Ala Thr Ser Val Asp Gly Gln Lys
        755                 760

<210> SEQ ID NO 2
<211> LENGTH: 876
<212> TYPE: PRT
<213> ORGANISM: Paenibacillus sp.

<400> SEQUENCE: 2

Met Asn Arg His Val Leu Leu His Pro Tyr Leu His Arg Lys Ala Leu
1               5                   10                  15

Pro Leu Leu Leu Ala Leu Thr Leu Thr Gly Ile Ala Leu Phe Pro
            20                  25                  30

Ala Ser Thr Ala Gln Ala Ala Thr Thr Val Thr Ser Met Thr Tyr Phe
        35                  40                  45

Ser Ala Asn Asp Gly Pro Val Ile Ser Lys Ser Gly Val Gly Gln Ala
    50                  55                  60

Ser Tyr Gly Phe Val Met Pro Ile Phe Asn Gly Gly Ala Ala Thr Trp
65                  70                  75                  80

Asn Asp Val Ala Asp Asp Val Gly Val Arg Val Lys Val Gly Gly Ser
                85                  90                  95

Trp Val Asp Ile Asp Ser Val Gly Gly Tyr Val Tyr Asn Gln Asn Trp
            100                 105                 110
```

```
Gly His Trp Asn Asp Ser Gly Thr Tyr Gly Tyr Trp Phe Thr Leu Ser
        115                 120                 125

Ala Thr Thr Glu Leu Gln Leu Tyr Ser Lys Ala Asn Ser Ser Val Thr
130                 135                 140

Leu Asn Tyr Thr Leu Val Phe Gln Asn Val Asn Glu Thr Thr Ile Thr
145                 150                 155                 160

Ser Met Thr Pro Thr Gln Gly Pro Gln Leu Thr Ala Gly Tyr Thr Gly
                165                 170                 175

Gly Ala Gly Phe Thr Tyr Pro Val Phe Asn Asn Asp Pro Ser Ile Pro
                180                 185                 190

Tyr Ala Ala Val Ala Gly Asp Leu Lys Val Tyr Val Lys Pro Val Ala
                195                 200                 205

Ser Ser Thr Trp Ile Asp Ile Asp Asn Asn Ala Ala Ser Gly Trp Ile
        210                 215                 220

Tyr Asp Ser Asn Phe Gly Gln Phe Thr Glu Gly Gly Gly Tyr Trp
225                 230                 235                 240

Phe Thr Val Thr Glu Ser Ile Asn Val Lys Leu Glu Ser Arg Thr Ser
                245                 250                 255

Ser Ala Asn Val Val Tyr Thr Ile Asn Phe Pro Gln Pro Thr Arg Ser
                260                 265                 270

Ser Tyr Thr Leu Ser Ala Tyr Asp Gly Thr Thr Tyr Ser Ala Asp Ala
        275                 280                 285

Ser Gly Ala Ile Gly Ile Pro Leu Pro Arg Ile Asp Gly Thr Pro Ala
        290                 295                 300

Ile Gly Ser Glu Leu Gly Asn Phe Val Tyr Gln Ile Tyr Arg Asn Gly
305                 310                 315                 320

Gln Trp Val Glu Met Ser Asn Ser Ala Gln Ser Ser Phe Val Tyr Ser
                325                 330                 335

Ala Asn Gly Tyr Asn Asn Met Ser Asp Ala Asn Gln Trp Gly Tyr Trp
                340                 345                 350

Ala Asp Tyr Ile Tyr Gly Leu Trp Phe Arg Pro Ile Gln Glu Asp Met
        355                 360                 365

Gln Ile Arg Ile Gly Tyr Pro Leu Asn Gly Gln Ser Gly Gly Ser Val
        370                 375                 380

Gly Ser Asn Phe Val Thr Tyr Thr Leu Ile Gly Asn Pro Asn Ala Pro
385                 390                 395                 400

Arg Pro Asp Val Ser Asp Gln Gly Asp Val Glu Ile Gly Thr Pro Thr
                405                 410                 415

Asp Pro Ala Ile Ala Gly Trp Asn Leu Tyr Trp Gln Asp Glu Phe Ala
                420                 425                 430

Gly Ser Ala Leu Asp Leu Asn Lys Trp Asn Tyr Glu Thr Gly Tyr Tyr
        435                 440                 445

Ile Gly Asn Asp Pro Asn Leu Trp Gly Trp Gly Asn Ala Glu Met Gln
450                 455                 460

His Tyr Thr Thr Ser Thr Gln Asn Val Phe Val Ala Asp Gly Lys Leu
465                 470                 475                 480

Asn Ile Arg Ala Leu His Asp Tyr Gln Ser Phe Pro Gln Asp Pro Asn
                485                 490                 495

Arg Tyr Ala Thr Tyr Ser Ser Gly Lys Ile Asn Thr Lys Asp Asn Met
                500                 505                 510

Ser Leu Gln Tyr Gly Arg Val Asp Ile Arg Ala Lys Leu Pro Thr Gly
        515                 520                 525
```

Asp Gly Val Trp Pro Ala Leu Trp Met Leu Pro Glu Asp Ser Val Tyr
530                 535                 540

Gly Ala Trp Ala Ala Ser Gly Glu Ile Asp Ile Met Glu Ala Lys Gly
545                 550                 555                 560

Arg Leu Pro Gly Thr Thr Ser Gly Ala Ile His Tyr Gly Gly Gln Trp
                565                 570                 575

Pro Val Asn Arg Tyr Leu Ala Gly Glu Cys Tyr Leu Pro Gln Gly Thr
            580                 585                 590

Thr Phe Ala Asp Asp Phe Asn Val Tyr Thr Met Ile Trp Glu Glu Asp
        595                 600                 605

Asn Met Lys Trp Tyr Val Asn Gly Glu Phe Phe Lys Val Thr Arg
610                 615                 620

Glu Gln Trp Tyr Ser Val Ala Ala Pro Asn Asn Pro Asp Ala Pro Phe
625                 630                 635                 640

Asp Gln Pro Phe Tyr Leu Ile Met Asn Leu Ala Val Gly Gly His Phe
                645                 650                 655

Asp Gly Gly Arg Thr Pro Asp Pro Ser Asp Ile Pro Ala Thr Met Gln
            660                 665                 670

Ile Asp Tyr Val Arg Val Tyr Lys Glu Gly Ala Gly Gly Pro Gly
        675                 680                 685

Asn Pro Gly Gly Asn Val Ala Val Thr Gly Val Ser Val Thr Pro Ala
690                 695                 700

Thr Ala Gln Val Gln Val Gly Gln Thr Val Ser Leu Ser Ala Asn Val
705                 710                 715                 720

Ala Pro Ala Asn Ala Thr Asn Lys Gln Val Thr Trp Ser Val Ala Asn
                725                 730                 735

Gly Ser Ile Ala Ser Val Ser Ala Ser Gly Val Val Ser Gly Leu Ala
            740                 745                 750

Ala Gly Thr Thr Thr Val Thr Ala Thr Thr Ala Asp Gly Asn Arg Thr
        755                 760                 765

Ala Ser Ala Thr Ile Thr Val Val Pro Pro Thr Thr Thr Val Ile
770                 775                 780

Ile Gly Asp Ser Val Arg Gly Ile Arg Lys Thr Gly Asp Asn Leu Leu
785                 790                 795                 800

Phe Tyr Val Asn Gly Ala Thr Tyr Ala Asp Leu His Tyr Lys Val Asn
                805                 810                 815

Gly Gly Gly Gln Pro Asn Val Ala Met Thr His Thr Gly Gly Asn
            820                 825                 830

Tyr Thr Tyr Pro Val His Gly Leu Gln Gln Gly Asp Thr Val Glu Tyr
        835                 840                 845

Phe Phe Thr Tyr Asn Pro Gly Asn Gly Ala Leu Asp Thr Pro Trp Gln
850                 855                 860

Thr Tyr Val His Gly Val Thr Gln Gly Val Val Glu
865                 870                 875

<210> SEQ ID NO 3
<211> LENGTH: 482
<212> TYPE: PRT
<213> ORGANISM: Zobellia galactanivorans

<400> SEQUENCE: 3

Met Lys Lys Ile Ile Thr Tyr Leu Leu Met Val Leu Cys Phe Gly Met
1               5                   10                  15

Thr Pro Ile Leu Ser Ala Gln Asp Tyr Asn Leu Val Trp Gln Asp Glu
            20                  25                  30

```
Phe Asp Asp Gly Ile Gly Pro Asp Trp Val Phe Glu Thr Gly Met Gly
         35                  40                  45

Tyr Asn Gly Trp Gly Asn Asn Glu Leu Gln Tyr Tyr Arg Arg Glu Asn
 50                  55                  60

Ala Ala Val Glu Asn Gly Asn Leu Val Ile Thr Ala Lys His Glu Asn
 65                  70                  75                  80

Phe Gly Gly Ala Gln Tyr Thr Ser Ala Arg Met Lys Thr Gln Gly Arg
                 85                  90                  95

Lys Ser Phe Lys Tyr Gly Lys Ile Glu Ala Arg Ile Ala Leu Pro Ser
                100                 105                 110

Gly Gln Gly Leu Trp Pro Ala Phe Trp Met Leu Gly Asn Asn Ile Thr
                115                 120                 125

Ser Val Ser Trp Pro Ala Cys Gly Glu Ile Asp Ile Met Glu Arg Ile
    130                 135                 140

Asn Asn Ala Leu Gln Thr His Gly Thr Ile His Trp Ser Asp Gln Asn
145                 150                 155                 160

Gly Asp His Ala Ser Tyr Gly Asp Asp Val Gly Val Ser Asp Pro Gly
                165                 170                 175

Gln Tyr His Ile Tyr Ser Val Glu Trp Asp Ala Asn Ser Ile Lys Trp
                180                 185                 190

Phe Val Asp Gly Gln Gln Phe Asn Glu Val Asp Ile Ser Asn Gly Val
                195                 200                 205

Asn Gly Thr Gly Glu Phe Gln Asn Glu Phe Phe Ile Leu Leu Asn Met
    210                 215                 220

Ala Val Gly Gly Asp Trp Pro Gly Phe Asp Val Asp Gln Ser Lys Leu
225                 230                 235                 240

Pro Ala Gln Met Leu Val Asp Tyr Val Arg Val Tyr Gln Lys Gly Asp
                245                 250                 255

Asp Asn Asp Ser Ala Asn Thr Leu Lys Ile Glu Ala Glu Ser Tyr Leu
                260                 265                 270

Tyr Ser Asn Asp Val Gln Lys Glu Pro Cys Ser Glu Gly Gly Glu Asn
    275                 280                 285

Val Gly Tyr Ile Asn Asn Gly Ser Trp Met Ser Tyr Pro Gly Ile Asn
    290                 295                 300

Phe Pro Ser Ser Gly Asn Tyr Leu Ile Glu Tyr Arg Val Ala Ser Ala
305                 310                 315                 320

Val Asp Gly Gly Arg Phe Ser Ser Asp Leu Glu Ala Gly Glu Thr Val
                325                 330                 335

Leu Gly Glu Leu Ser Val Pro Asn Thr Gly Gly Trp Gln Asn Trp Thr
                340                 345                 350

Thr Val Ser Gln Thr Val Asn Val Ser Ala Gly Thr Tyr Gln Phe Gly
                355                 360                 365

Leu Tyr Ser Ile Ser Gly Gly Trp Asn Ile Asn Trp Ile Arg Ile Thr
    370                 375                 380

Lys Gln Gly Thr Ala Ser Ala Ala Thr Ala Leu Asn Ser Ser Leu Ile
385                 390                 395                 400

Ala Ser Asp Asn Gly Ile Ser Gln Glu Ile Arg Val Tyr Pro Asn Pro
                405                 410                 415

Phe Thr Glu Tyr Val Ser Val Asn Phe Asp Gly Glu Ala Ala Asn Leu
                420                 425                 430

Thr Leu Gln Asp Met Leu Gly Thr Val Ile Phe Ser Lys Ser Gly Val
                435                 440                 445
```

Ser Ala Asp Glu Ser Val Asp Leu Ser Gly Leu Lys Ser Gly Val Tyr
            450                 455                 460

Phe Leu Thr Ile Glu Gln Asp Gly Lys Ser Thr Val Arg Gln Leu Ile
465                 470                 475                 480

Lys Glu

<210> SEQ ID NO 4
<211> LENGTH: 449
<212> TYPE: PRT
<213> ORGANISM: Paenibacillus sp.

<400> SEQUENCE: 4

Met Lys Gln Lys Gly Met Arg Tyr Leu Leu Val Leu Ser Leu Leu Leu
1               5                   10                  15

Thr Cys Trp Ser Val Phe Gly Thr Arg Ala Glu Ala Ala Asp Tyr Thr
            20                  25                  30

Gln Gly Val Glu Leu Ser Gly Ser Thr Ala Thr Val Trp Phe Lys Ser
        35                  40                  45

Ala Val Asn Thr Ser Trp Val Asp Val His Tyr Arg Val Asn Gly Gly
    50                  55                  60

Glu Gln Gln Asn Val Arg Met Ser Tyr His Ala Gly Lys Ser Arg Tyr
65                  70                  75                  80

Glu Gln Ala Ile Ser Gly Ile Ala Ala Gly His Val Ile Thr Tyr Ser
                85                  90                  95

Phe Thr Tyr Asn Asn Gly Ile Pro Ala Tyr Asp Thr Gly Val Phe Ser
            100                 105                 110

Tyr Thr Ala Gly Ser Thr Pro Pro Ser Ser Gly Ser Ile Tyr
        115                 120                 125

Asp Ile Leu Pro Ser Thr Ile Pro Met Pro Asn Gly Ala Val Ser
130                 135                 140

Val Lys Ile Met Asn Gly Thr His Gly Ala Tyr Thr Asp Gln Gln Ile
145                 150                 155                 160

Tyr Trp Gly Val Leu Gly Ile Asn Pro Val Asn Asn Gln Trp Ser Tyr
                165                 170                 175

Leu Asp Leu Asn Gly Asn Leu Ile Pro Ile Ser Ser Ala Leu Asn Asp
            180                 185                 190

Ala Pro Gly His Leu Thr Lys Asn Gly Ile Asn Tyr Ala Asn Ile Tyr
        195                 200                 205

His Lys Val Asn Asp Ala Ser Trp Val Thr Leu Pro Gln Ile Thr Ser
210                 215                 220

Gly Arg Met Phe Leu Ser Val Gly Thr Pro Leu Tyr Leu Lys Thr Phe
225                 230                 235                 240

Asn Asp Gly Phe Ala Gly Pro Asp Leu Asn Asn Pro Thr Asp Pro Asn
                245                 250                 255

Arg Asp Ile Tyr Phe Asp Phe Val Glu Phe Thr Ile Asp Ala Ala Gly
            260                 265                 270

Tyr His Gly Asn Thr Thr Arg Val Asp Gly Phe Gly Phe Pro Leu Gln
        275                 280                 285

His Arg Leu Val Asn Lys Ser Gly Ser Phe Asp Gln Thr Val Gly Glu
290                 295                 300

Leu Glu Ser Glu Thr Arg Asn Gly Ile Phe Ala Lys Phe Gln Ala Glu
305                 310                 315                 320

Val Pro Ala Ala Phe Lys Ser Leu Ala Thr Ile Gln Ala Pro Tyr Arg
                325                 330                 335

```
Ile Val Ala Pro Ile His Gly Ser Phe Ala Gln Gly Ala Asn Ala
            340                 345                 350
Asn Tyr Phe Gly Gly Tyr Ala Pro Tyr Ser Thr Gln Asp Ile Phe Arg
            355                 360                 365
Cys Asp Gly Ala Leu Thr Asp Ala Ala Thr Cys Ala Ala Ile Gln Arg
        370                 375                 380
His Val Tyr Thr Ala Asn Asp Trp Asn Asn Val Ser Asn Tyr Tyr Gln
385                 390                 395                 400
Ala Ala Pro Ala Asn Tyr Tyr Ala Lys Phe Trp His Asp His Ser Ile
                405                 410                 415
Asn Arg Leu Ala Tyr Gly Phe Pro Tyr Asp Asp Val Asn Gly Gln Ala
            420                 425                 430
Ala Tyr Leu Glu Val Gly Asp Pro Lys Gly Leu Ile Ile Arg Ile Gly
        435                 440                 445
Trp

<210> SEQ ID NO 5
<211> LENGTH: 641
<212> TYPE: PRT
<213> ORGANISM: Thermotoga petrophila

<400> SEQUENCE: 5

Met Ser Arg Leu Val Phe Ala Leu Leu Leu Phe Pro Val Phe Ile Leu
1               5                   10                  15
Ala Gln Asn Ile Leu Gly Asn Ala Ser Phe Asp Glu Pro Ile Leu Ile
                20                  25                  30
Ala Gly Met Asp Ile Asp Pro Pro Ala Glu Asp Gly Ser Ile Asn Thr
            35                  40                  45
Glu Gly Asn Trp Val Phe Phe Thr Asn Ser Asn Gly Glu Gly Thr Ala
        50                  55                  60
Arg Val Glu Asn Gly Val Leu Val Glu Ile Thr Asn Gly Gly Asp
65                  70                  75                  80
His Thr Trp Ser Val Gln Ile Ile Gln Ala Pro Ile Arg Val Glu Lys
                85                  90                  95
Leu His Lys Tyr Arg Val Ser Phe Arg Ala Arg Ala Ser Ser Gln Arg
            100                 105                 110
Asn Val Gly Val Lys Ile Gly Gly Thr Ala Gly Arg Ser Trp Ala Ala
        115                 120                 125
Tyr Asn Pro Gly Thr Asp Glu Ser Gly Gly Met Val Phe Glu Leu Gly
    130                 135                 140
Thr Asp Trp Gln Thr Tyr Glu Phe Glu Phe Val Met Arg Gln Glu Thr
145                 150                 155                 160
Asp Glu Asn Ala Arg Phe Glu Phe Gln Leu Gly Arg Tyr Thr Gly Thr
                165                 170                 175
Val Trp Ile Asp Asp Val Val Met Glu Asp Ile Gly Val Leu Glu Val
            180                 185                 190
Ser Gly Glu Glu Asn Glu Ile Tyr Thr Glu Glu Asp Glu Asp Lys Val
        195                 200                 205
Glu Asp Trp Gln Leu Val Trp Ser Gln Glu Phe Asp Asp Gly Val Ile
    210                 215                 220
Asp Pro Asn Ile Trp Asn Phe Glu Ile Gly Asn Gly His Ala Lys Gly
225                 230                 235                 240
Ile Pro Gly Trp Gly Asn Gly Glu Leu Glu Tyr Tyr Thr Asp Glu Asn
                245                 250                 255
```

```
Ala Phe Val Glu Asn Gly Cys Leu Val Ile Glu Ala Arg Lys Glu Gln
                260                 265                 270

Val Ser Asp Glu Tyr Gly Thr Tyr Asp Tyr Thr Ser Ala Arg Met Thr
            275                 280                 285

Thr Glu Gly Lys Phe Glu Ile Lys Tyr Gly Lys Ile Glu Ile Arg Ala
        290                 295                 300

Lys Leu Pro Lys Gly Lys Gly Ile Trp Pro Ala Leu Trp Met Leu Gly
305                 310                 315                 320

Asn Asn Ile Gly Glu Val Gly Trp Pro Thr Cys Gly Glu Ile Asp Ile
                325                 330                 335

Met Glu Met Leu Gly His Asp Thr Arg Thr Val Tyr Gly Thr Ala His
            340                 345                 350

Gly Pro Gly Tyr Ser Gly Gly Ala Ser Ile Gly Val Ala Tyr His Leu
        355                 360                 365

Pro Glu Gly Val Pro Asp Phe Ser Glu Asp Phe His Ile Phe Ser Ile
370                 375                 380

Glu Trp Asp Glu Asp Glu Val Glu Trp Tyr Val Asp Gly Gln Leu Tyr
385                 390                 395                 400

His Val Leu Ser Lys Asp Glu Leu Ala Glu Leu Gly Leu Glu Trp Val
                405                 410                 415

Phe Asp His Pro Phe Phe Leu Ile Leu Asn Val Ala Val Gly Gly Tyr
            420                 425                 430

Trp Pro Gly Tyr Pro Asp Glu Thr Thr Gln Phe Pro Gln Arg Met Tyr
        435                 440                 445

Ile Asp Tyr Ile Arg Val Tyr Glu Asp Lys Asn Pro Glu Thr Ile Thr
450                 455                 460

Gly Glu Val Asp Asp Cys Glu Tyr Glu Gln Ala Gln Gln Ala Gly
465                 470                 475                 480

Pro Glu Val Thr Tyr Glu Arg Ile Asn Asn Gly Thr Phe Asp Glu Pro
                485                 490                 495

Ile Val Asn Asp Gln Ala Asn Asn Pro Asp Glu Trp Phe Ile Trp Gln
            500                 505                 510

Ala Gly Asp Tyr Gly Ile Ser Gly Ala Arg Val Ser Asp Tyr Gly Val
        515                 520                 525

Arg Asp Gly Tyr Ala Tyr Ile Thr Ile Ala Asp Pro Gly Thr Asp Thr
530                 535                 540

Trp His Ile Gln Phe Asn Gln Trp Ile Gly Leu Tyr Arg Gly Lys Thr
545                 550                 555                 560

Tyr Thr Ile Ser Phe Lys Ala Lys Ala Asp Thr Pro Arg Pro Ile Asn
                565                 570                 575

Val Lys Ile Leu Gln Asn His Asp Pro Trp Thr Asn Tyr Phe Ala Gln
            580                 585                 590

Thr Val Asn Leu Thr Ala Asp Trp Gln Thr Phe Thr Phe Thr Tyr Thr
        595                 600                 605

His Pro Asp Asp Ala Asp Glu Val Val Gln Ile Ser Phe Glu Leu Gly
610                 615                 620

Lys Glu Thr Ala Thr Thr Ile Tyr Phe Asp Asp Val Ser Val Ser Pro
625                 630                 635                 640

Gln

<210> SEQ ID NO 6
<211> LENGTH: 286
<212> TYPE: PRT
<213> ORGANISM: Rhodothermus marinus
```

-continued

```
<400> SEQUENCE: 6

Met Cys Thr Met Pro Leu Met Lys Leu Lys Lys Met Met Arg Arg Thr
1               5                   10                  15

Ala Phe Leu Leu Ser Val Leu Ile Gly Cys Ser Met Leu Gly Ser Asp
            20                  25                  30

Arg Ser Asp Lys Ala Pro His Trp Glu Leu Val Trp Ser Asp Glu Phe
        35                  40                  45

Asp Tyr Ser Gly Leu Pro Asp Pro Glu Lys Trp Asp Tyr Asp Val Gly
    50                  55                  60

Gly His Gly Trp Gly Asn Gln Glu Leu Gln Tyr Tyr Thr Arg Ala Arg
65                  70                  75                  80

Ile Glu Asn Ala Arg Val Gly Gly Val Leu Ile Ile Glu Ala Arg
                85                  90                  95

His Glu Pro Tyr Glu Gly Arg Glu Tyr Thr Ser Ala Arg Leu Val Thr
            100                 105                 110

Arg Gly Lys Ala Ser Trp Thr Tyr Gly Arg Phe Glu Ile Arg Ala Arg
        115                 120                 125

Leu Pro Ser Gly Arg Gly Thr Trp Pro Ala Ile Trp Met Leu Pro Asp
130                 135                 140

Arg Gln Thr Tyr Gly Ser Ala Tyr Trp Pro Asp Asn Gly Glu Ile Asp
145                 150                 155                 160

Ile Met Glu His Val Gly Phe Asn Pro Asp Val His Gly Thr Val
                165                 170                 175

His Thr Lys Ala Tyr Asn His Leu Leu Gly Thr Gln Arg Gly Gly Ser
            180                 185                 190

Ile Arg Val Pro Thr Ala Arg Thr Asp Phe His Val Tyr Ala Ile Glu
        195                 200                 205

Trp Thr Pro Glu Glu Ile Arg Trp Phe Val Asp Asp Ser Leu Tyr Tyr
210                 215                 220

Arg Phe Pro Asn Glu Arg Leu Thr Asp Pro Ala Asp Trp Arg His
225                 230                 235                 240

Trp Pro Phe Asp Gln Pro Phe His Leu Ile Met Asn Ile Ala Val Gly
                245                 250                 255

Gly Ala Trp Gly Gly Gln Gln Gly Val Asp Pro Glu Ala Phe Pro Ala
            260                 265                 270

Gln Leu Val Val Asp Tyr Val Arg Val Tyr Arg Trp Val Glu
        275                 280                 285

<210> SEQ ID NO 7
<211> LENGTH: 291
<212> TYPE: PRT
<213> ORGANISM: Trichoderma sp.

<400> SEQUENCE: 7

Met Trp Ser Pro Lys Val Ala Ala Ala Val Leu Ala Phe Val Gly Ala
1               5                   10                  15

Thr Asn Ala Trp Gln Pro Pro Thr Tyr Ser Gly Phe Asn Leu Val Trp
            20                  25                  30

Thr Asp Thr Phe Ala Gly Gly Thr Ser Pro Asn Gln Asn Asn Trp
        35                  40                  45

Asn Ile Ile Thr Gly Asn Leu Asn Val Asn Ala Glu Gln Glu Thr Tyr
    50                  55                  60

Ser Ser Ser Thr Ala Asn Val Gln Leu Ser Gly Gly Ser Thr Leu Gln
65                  70                  75                  80
```

```
Leu Val Pro Trp Arg Asp Ser Ser Lys Gly Thr Ser Thr Phe Gly Gly
                85                  90                  95

Trp Thr Ser Gly Arg Leu Glu Ser Lys Tyr Thr Phe Thr Pro Ala Ala
            100                 105                 110

Gly Lys Val Thr Arg Leu Glu Ala Ala Ile Arg Phe Gly Ser Asn Ala
        115                 120                 125

Gln Ala Asn Lys Gln Gly Ile Trp Pro Ala Phe Trp Met Leu Gly Asp
    130                 135                 140

Ser Leu Arg Gln Pro Gly Gly Ser Trp Pro Asn Cys Gly Glu Ile Asp
145                 150                 155                 160

Ile Met Glu Thr Val Asp Gly Gln Ala Thr Gly His Gly Thr Leu His
                165                 170                 175

Cys Asp Val Tyr Pro Gly Gly Ile Cys Asn Glu Gly Asn Gly Ile Gly
            180                 185                 190

Gly Pro Val Asn Ile Ala Asn Val Asn Asp Trp His Ala Trp Arg Val
        195                 200                 205

Glu Ile Asp Arg Thr Pro Ser Ser Trp Gln Ser Glu Thr Leu Thr Trp
    210                 215                 220

Ser Leu Asp Gly Thr Ile Tyr Phe Gln Ile Thr Gly Ser Arg Ile Gly
225                 230                 235                 240

Asn Gln Gly Val Trp Asn Asn Ile Ala His Ser Pro Leu Phe Phe Ile
                245                 250                 255

Leu Asn Val Ala Val Gly Gly Asn Trp Pro Gly Asn Pro Asn Ser Ala
            260                 265                 270

Thr Leu Asp Gly Tyr Gly Ser Met Met Glu Val Gly Tyr Val Ala Gln
        275                 280                 285

Tyr Ser Thr
    290

<210> SEQ ID NO 8
<211> LENGTH: 490
<212> TYPE: PRT
<213> ORGANISM: Bacillus hemicellulosilyticus

<400> SEQUENCE: 8

Met Arg Asn Phe Gly Lys Leu Ile Val Ser Ser Cys Leu Leu Phe Ser
1               5                   10                  15

Phe Phe Leu Phe Ala Ser Asp Gly His Ser Gln Thr His Ser Gly Phe
            20                  25                  30

Tyr Ile Glu Gly Ser Thr Leu Tyr Asp Ala Asn Gly Glu Pro Phe Val
        35                  40                  45

Met Arg Gly Ile Asn His Gly His Ala Trp Tyr Lys His Asp Ser Asn
    50                  55                  60

Val Ala Ile Pro Ala Ile Ala Asn Gln Gly Ala Asn Thr Ile Arg Ile
65                  70                  75                  80

Val Leu Ser Asp Gly Gly Gln Trp Ala Lys Asp Ile Asn Thr Leu
                85                  90                  95

Asn Gln Val Leu Asp Leu Ala Glu Glu His Glu Met Ile Ala Val Val
            100                 105                 110

Glu Val His Asp Ala Thr Gly Ser Asn Ser Met Ala Asp Leu Asn Arg
        115                 120                 125

Ala Val Asp Tyr Trp Ile Glu Met Lys Asp Ala Leu Ile Gly Lys Glu
    130                 135                 140

Asp Arg Val Ile Ile Asn Ile Ala Asn Glu Trp Tyr Gly Ala Trp Asp
```

```
            145                 150                 155                 160
Gly Gln Gly Trp Ala Asn Gly Tyr Lys Glu Val Ile Pro Arg Leu Arg
                165                 170                 175

Asn Ala Gly Phe Thr His Thr Leu Met Val Asp Ala Ala Gly Trp Gly
                180                 185                 190

Gln Tyr Pro Gln Ser Ile His Asp Tyr Gly Gln Glu Val Phe Asn Ala
                195                 200                 205

Asp Pro Leu Ala Asn Thr Met Phe Ser Ile His Met Tyr Glu Tyr Ala
            210                 215                 220

Gly Gly Asn Ala Ser Met Val Gln Ser Asn Ile Asp Gly Val Val Asp
225                 230                 235                 240

Gln Gly Leu Ala Leu Val Ile Gly Glu Phe Gly His Met His Thr Asp
                245                 250                 255

Gly Asp Val Asp Glu Ala Thr Ile Leu Ser Tyr Ser Gln Gln Arg Gly
                260                 265                 270

Val Gly Trp Leu Ala Trp Ser Trp Lys Gly Asn Gly Thr Gln Trp Glu
                275                 280                 285

Tyr Leu Asp Leu Ser Tyr Asp Trp Gln Gly Thr Asn Leu Thr Ser Trp
            290                 295                 300

Gly Asn Thr Ile Val His Gly Pro Asn Gly Leu Leu Glu Thr Ser Ile
305                 310                 315                 320

Pro Ser Ser Ile Phe His Thr Ala Pro Asn Asn Gly Asp Pro Pro
                325                 330                 335

His Asn Gly Asn Glu Thr Ile Leu Tyr Asp Phe Glu His Gly Thr Gln
                340                 345                 350

Gly Trp Ser Gly Ser Ser Leu Leu Gly Gly Pro Trp Thr Thr Asn Glu
                355                 360                 365

Trp Ser Thr Asn Gly Asn His Ser Leu Lys Ala Asp Ile Phe Leu Ser
            370                 375                 380

Ala Asn Ser Lys His Glu Leu Ala Lys Val Glu Asn Arg Asn Leu Ser
385                 390                 395                 400

Gly Tyr Ser Thr Leu Gln Ala Thr Val Arg His Ala His Trp Gly Asn
                405                 410                 415

Val Gly Asn Leu Thr Ala Arg Met Tyr Val Lys Thr Gly Ser Asn Tyr
                420                 425                 430

Ser Trp Phe Asn Gly Asp Pro Ile Pro Val Asn Ser Ala Asn Gly Thr
            435                 440                 445

Thr Val Thr Leu Pro Leu Ser Ser Ile Pro Asn Leu Asn Asp Val Lys
450                 455                 460

Glu Ile Gly Val Glu Phe Ile Gly Ala Ser Ser Ser Asn Gly Gln Thr
465                 470                 475                 480

Ala Ile Tyr Leu Asp His Val Thr Ile Gln
                485                 490

<210> SEQ ID NO 9
<211> LENGTH: 1050
<212> TYPE: PRT
<213> ORGANISM: Paenibacillus sp-62047

<400> SEQUENCE: 9

Ile Ala Gly Val Val Gln Ser Val Asn Val Ser Gln Ala Gly Tyr Ser
1               5                   10                  15

Ser Asn Asp Phe Lys Thr Ala Thr Val Thr Ala Ser Asp Lys Leu Ser
            20                  25                  30
```

-continued

```
Asp Thr Ser Tyr Gln Ile Leu Gln Gly Thr Thr Val Ile Ala Thr Gly
         35                  40                  45

Thr Met Lys Asp Glu Gly Tyr Val Trp Gly Lys Tyr Val Tyr Ser Ile
 50                  55                  60

Asp Phe Ser Ser Val Thr Ala Thr Gly Thr Asn Phe Thr Ile Arg Ser
 65                  70                  75                  80

Asn Gly Val Ser Ser Tyr Thr Phe Pro Ile Gln Thr Asn Met Trp Asn
                 85                  90                  95

Glu Tyr Lys Asp Glu Met Thr Ala Phe Tyr Arg Leu Leu Arg Thr Thr
            100                 105                 110

Asp Thr Phe Ala Ala Tyr Pro Ala Gly Tyr Ser Asn Ile Ala Pro Ser
            115                 120                 125

Asn Lys Ile Leu His Pro Asp Ser Phe Leu Asp Asp Ala Phe Ser Pro
130                 135                 140

Asp Arg Thr Thr His Tyr Asp Leu Thr Gly Gly Trp Phe Asp Ala Gly
145                 150                 155                 160

Asp Tyr Gly Lys Tyr Gly Gly Asn Gln Trp Val Gln Gly Asn Ile Ala
                165                 170                 175

Ile Ser Tyr Leu Arg His Ala Ser Ser Ala Ala Val Asn Phe Asp Lys
            180                 185                 190

Asp Thr Asn Gly Ile Pro Asp Leu Val Asp Glu Ala Ile Phe Gly Ser
            195                 200                 205

Gln Tyr Leu Val Lys Phe Ala Asn Gln Leu Gly Gly Ala Ile His Asn
            210                 215                 220

Ile Leu Arg Lys Gly Gly Phe Val Leu Pro His Lys Val Thr Asp Asn
225                 230                 235                 240

Val Pro Gly Asn Thr Asp Asp Arg Ala Leu Glu Ala Val Glu Ala Val
                245                 250                 255

Gly Gly Ser Gly Lys Ser Ser Gly Ser Leu Ala Ala Thr Ala Arg Ala
            260                 265                 270

Ile Arg Thr Ala Ile Ala Gly Gly Lys Val Ala Ala Asn Lys Val Ala
            275                 280                 285

Gln Leu Gln Thr Leu Ala Asn Glu Phe Gln Ala Ala Ile Ile Phe
            290                 295                 300

Tyr Asn Tyr Thr Leu Thr His Gln Ser Gly Asn His Gly Ser Tyr Gly
305                 310                 315                 320

Thr Met Asn Asn Gly Gly Ile Ala Asn Pro Leu Leu Trp Ala Glu Val
                325                 330                 335

Gln Leu Tyr Leu Leu Thr Gly Asp Ala Ala Tyr Lys Thr Gln Ala Gln
            340                 345                 350

Thr Arg Ile Asn Ala Ile Asn Glu Ala Tyr Val Ser Ser Thr Asn Tyr
            355                 360                 365

Trp Asp Met His Pro Ile Ala Leu Ala Glu Phe Tyr Pro Val Ala Asp
            370                 375                 380

Ser Ala Ile Lys Thr Lys Ile Gln Ser Ile Leu Lys His Gln Ala Tyr
385                 390                 395                 400

Tyr Phe Ile Thr Leu Met Asp Glu Thr Pro Tyr Gly Val Leu Asn Gln
                405                 410                 415

Phe Gly Asn Phe Gly Val Asn Glu Pro His Ala Ser Tyr Met Ala Asp
            420                 425                 430

Leu Leu Arg Tyr Tyr Glu Leu Phe Asn Asp Pro Val Ala Leu Arg Ala
            435                 440                 445

Ala Lys Lys Ala Leu Tyr Trp Ile Val Gly Asn Asn Pro Trp Asn Ile
```

```
                450             455             460
Ser Trp Val Ser Gly Val Gly Ser Asn Phe Thr Asp Phe Leu His Thr
465                 470                 475                 480

Arg Leu Asp Glu Glu Ala Tyr Ser Gln Thr Asn Thr Gly Val Val Leu
                485                 490                 495

Pro Gly Ala Met Val Ser Gly Pro Asn Ile Lys Asp Pro Asn Asn Lys
            500                 505                 510

Leu Ser Ser Pro Trp Tyr Glu Asp Lys Pro Ile Trp Ala Asp Asp
        515                 520                 525

Thr Asn Gln Trp Arg Tyr Asn Glu Tyr Ser Val Ser Ile Gln Thr Gly
    530                 535                 540

Leu Phe Tyr Thr Ile Met Gly Leu Ser Ala Leu Gly Gly Asn Ala Ser
545                 550                 555                 560

Thr Gly Gly Ala Glu Pro Val Lys Leu Pro Ile Thr Trp Pro Ile Ile
                565                 570                 575

Gly Asp Tyr Val Thr Gly Asp Val Thr Val Phe Ala Gln Pro Glu Gly
            580                 585                 590

Ser Leu Ser Asn Val Ser Ala Asn Gly Ile Val Leu Ser Pro Ser Asp
        595                 600                 605

Gly Val Tyr Thr Thr Thr Val Ser Thr Ser Ala Asp Ala Pro Tyr Thr
    610                 615                 620

Glu Arg Lys Val Gln Ile Lys Gly Thr Asp Asp Ser Gly Phe Thr Thr
625                 630                 635                 640

Tyr Ser Asn Thr His Phe Thr Val Ala Pro Ala Leu Pro Asp Pro Ser
                645                 650                 655

His Pro Leu Leu Phe Asp Asp Phe Asn Gln Lys Gly Ile Trp Gly Ser
            660                 665                 670

Gln Lys Leu Asp Trp Val Asn Trp Tyr Asn Gln Asn Gly Gly Thr Ala
        675                 680                 685

Ser Tyr Thr Arg Thr Thr Val Asp Thr Arg Thr Val Gly Lys Phe Ala
    690                 695                 700

His Thr Pro Ala Ala Thr Thr Ser Lys Ala Lys Phe Gln Pro Trp Lys
705                 710                 715                 720

Tyr Asn Ala Asn Leu Asn Gly Tyr Arg Tyr Leu Asn Phe Thr Met Lys
                725                 730                 735

Asn Pro Gly Tyr Pro Asn Thr Lys Ile Arg Ile Ala Ala Asn Asp Gly
            740                 745                 750

Thr Lys Ser Val Asn Leu Thr Ser Gly Glu Val Ala Ile Ser Ser Thr
        755                 760                 765

Trp Thr Thr Tyr Gln Tyr Asp Leu Asn Leu His Pro Thr Leu Asn Lys
    770                 775                 780

Ser Asn Val Leu Ile Glu Val Trp Leu Ser Asn Pro Thr Ala Gly Ala
785                 790                 795                 800

Tyr Gly Glu Ile Leu Ile Asp Glu Ile Ser Ala Val Asn Thr Asn Ser
                805                 810                 815

Gly Thr Ala Pro Thr Leu Ser Ala Thr Gly Val Asn Ala Ser Ile Gly
            820                 825                 830

Asn Gln Ser Thr Val Phe Thr Tyr Thr Ala Thr Tyr Thr Asp Ala Asn
        835                 840                 845

Asn Gln Ala Pro Phe Asp Val Gln Val Val Ile Asp Gly Val Ile Arg
    850                 855                 860

Ser Met Thr Ala Ala Asp Pro Thr Asp Thr Thr Tyr Ser Asp Gly Arg
865                 870                 875                 880
```

```
Val Tyr Thr Tyr Ala Thr Thr Leu Pro Val Gly Thr His Lys Phe Tyr
                885                 890                 895

Phe Arg Thr Thr Asp Thr Thr Thr Asn Phe Val Ser Thr Ser Val Gln
            900                 905                 910

Thr Gly Pro Thr Val Ile Arg Asn Lys Leu Glu Ala Glu Val Leu Ser
        915                 920                 925

Ile Asn Leu Thr Asn Tyr Thr His Ala Val Lys Asp Asn Ala Asp Ala
    930                 935                 940

Ser Gly Gly Lys Tyr Arg Leu Phe Asn Gly Arg Gln Ala Asn Asp Tyr
945                 950                 955                 960

Ile Glu Tyr Ala Val Asn Val Pro Lys Ala Gly Thr Tyr Gln Val Ser
                965                 970                 975

Ala Arg Ala Met Arg Leu Ser Asp Asn Gly Ile Tyr Gln Leu Gln Ile
            980                 985                 990

Asn Gly Ser Asn Gln Gly Thr Pro Phe Asp Thr Tyr Gln Ser Ser Gly
        995                 1000                1005

Lys Tyr Leu Asp Tyr Ala Leu Gly Asn Val Thr Ile Thr Ser Pro
    1010                1015                1020

Gly Thr Gln Leu Phe Arg Phe Lys Val Thr Gly Lys Asn Ala Ser
    1025                1030                1035

Ser Leu Gly Tyr Lys Leu Pro Leu Asp Phe Ile Gln
    1040                1045                1050

<210> SEQ ID NO 10
<211> LENGTH: 1037
<212> TYPE: PRT
<213> ORGANISM: Paenibacillus sp.

<400> SEQUENCE: 10

Asp Glu Phe Asp Thr Leu Arg Glu Lys Tyr Lys Ala Met Leu Asn Gly
1               5                   10                  15

Gly Thr Thr Tyr Asn Leu Ser Asp Pro Asp Ile Ala Ala Arg Val Asn
            20                  25                  30

Ala Ile Thr Val Thr Ala Gln Gly Tyr Trp Asp Ser Met Leu Lys Asp
        35                  40                  45

Pro Asn Arg Asn Arg Leu Trp Asn Asp Ala Pro Phe Gly Ser Asp Ser
    50                  55                  60

Thr Ser Ile Thr Thr Thr Tyr Arg His Leu Tyr Asp Met Ala Leu Ala
65                  70                  75                  80

Tyr Thr Thr Tyr Gly Ser Ser Leu Gln Gly Asn Ala Ala Leu Lys Ala
                85                  90                  95

Asp Ile Ile Ser Gly Leu Asp Trp Met Asn Ala Asn Gln Phe Tyr Asn
            100                 105                 110

Gly Cys Ser Gln Tyr Gln Asn Trp Trp His Trp Gln Ile Gly Gly Pro
        115                 120                 125

Met Ala Leu Asn Asp Ile Val Ala Leu Met Tyr Thr Glu Leu Thr Ala
    130                 135                 140

Thr Gln Ile Ser Asn Tyr Met Ala Ala Ile Tyr Tyr Thr Gln Ala Ser
145                 150                 155                 160

Val Thr Met Thr Gly Ala Asn Arg Leu Trp Glu Ser Gln Val Ile Ala
                165                 170                 175

Ile Ser Gly Ile Leu Asn Lys Asp Ser Ala Arg Val Ala Ala Gly Arg
            180                 185                 190

Asp Gly Ile Ser Ala Leu Leu Pro Tyr Val Ala Lys Gly Asp Gly Phe
```

```
              195                 200                 205
Tyr Asn Asp Gly Ser Phe Val Gln His Thr Tyr Tyr Ala Tyr Asn Gly
210                 215                 220
Gly Tyr Gly Ser Glu Leu Leu Ser Gly Ile Ala Asp Leu Ile Phe Ile
225                 230                 235                 240
Leu Asn Gly Ser Ser Trp Gln Val Thr Asp Pro Asn Lys Asn Asn Val
                    245                 250                 255
Tyr Arg Trp Ile Tyr Asp Ser Tyr Glu Pro Phe Ile Tyr Lys Gly Asn
                260                 265                 270
Leu Met Asp Met Val Arg Gly Arg Glu Ile Ser Arg His Gly Leu Gln
                275                 280                 285
Asp Asp Lys Ala Ala Val Thr Val Met Ala Ser Ile Ile Arg Leu Ser
290                 295                 300
Gln Thr Ala Ala Ser Ala Asp Ala Thr Ala Phe Lys Arg Met Val Lys
305                 310                 315                 320
Tyr Trp Leu Leu Leu Asp Thr Asp Lys Thr Phe Leu Lys Ala Val Ser
                    325                 330                 335
Ile Asp Leu Ile Ile Ala Ala Asn Gln Leu Val Asn Asp Ser Thr Val
                340                 345                 350
Thr Ser Arg Gly Glu Leu Val Lys Tyr Lys Gln Phe Ser Gly Met Asp
                355                 360                 365
Arg Ala Val Gln Leu Arg Pro Gly Phe Gly Phe Gly Leu Ser Met Phe
370                 375                 380
Ser Ser Arg Ile Gly Asn Tyr Glu Ser Ile Asn Ala Glu Asn Asn Lys
385                 390                 395                 400
Gly Trp His Thr Gly Asp Gly Met Thr Tyr Leu Tyr Asn Thr Asp Leu
                    405                 410                 415
Ser Gln Phe Asn Asp His Phe Trp Ala Thr Val Asp Asn Tyr Arg Leu
                420                 425                 430
Pro Gly Thr Thr Val Leu Gln Asn Thr Thr Gln Thr Ala Asn Ser Arg
                435                 440                 445
Ser Asp Lys Ser Trp Ala Gly Gly Thr Asp Ile Leu Gly Gln Tyr Gly
450                 455                 460
Val Ser Gly Met Glu Leu His Thr Val Gly Lys Ser Leu Thr Ala Lys
465                 470                 475                 480
Lys Ser Trp Phe Met Phe Asp Asp Glu Ile Val Ala Leu Gly Ser Gly
                    485                 490                 495
Ile Ala Ser Thr Asp Gly Ile Ala Thr Glu Thr Ile Val Glu Asn Arg
                500                 505                 510
Lys Leu Asn Ser Ser Gly Asn Asn Ala Leu Ile Val Asn Gly Thr Ala
                515                 520                 525
Lys Pro Gly Ser Leu Gly Trp Ser Glu Thr Met Thr Gly Thr Asn Tyr
530                 535                 540
Ile His Leu Ala Gly Ser Val Pro Gly Ser Asp Ile Gly Tyr Tyr Phe
545                 550                 555                 560
Pro Gly Gly Ala Ala Val Lys Gly Leu Arg Glu Ala Arg Ser Gly Ser
                    565                 570                 575
Trp Ser Ser Leu Asn Ser Ser Ala Ser Trp Lys Asp Ser Thr Leu His
                580                 585                 590
Thr Arg Asn Phe Met Thr Leu Trp Phe Asp His Gly Met Asn Pro Thr
                595                 600                 605
Asn Gly Ser Tyr Ser Tyr Val Leu Leu Pro Asn Lys Thr Ser Ser Ala
610                 615                 620
```

-continued

Val Ala Ser Tyr Ala Ala Thr Pro Gln Ile Ser Ile Leu Glu Asn Ser
625                 630                 635                 640

Ser Ser Ala Gln Ala Val Lys Glu Thr Gln Leu Asn Val Thr Gly Ile
            645                 650                 655

Asn Phe Trp Asn Asp Glu Pro Thr Thr Val Gly Leu Val Thr Ser Asn
            660                 665                 670

Arg Lys Ala Ser Val Met Thr Lys Glu Thr Ala Ser Asp Phe Glu Ile
            675                 680                 685

Ser Val Ser Asp Pro Thr Gln Ser Asn Val Gly Thr Ile Tyr Ile Asp
            690                 695                 700

Val Asn Lys Ser Ala Thr Gly Leu Ile Ser Lys Asp Asn Glu Ile Thr
705                 710                 715                 720

Val Ile Gln Tyr Tyr Pro Thr Met Lys Phe Lys Val Asn Val Asn Asn
                725                 730                 735

Ser Gly Gly Lys Ser Tyr Lys Val Lys Phe Ser Leu Thr Gly Thr Pro
            740                 745                 750

Gly Ser Asn Pro Ser Pro Ile Pro Ile Pro Asn Pro Tyr Glu Ala Glu
            755                 760                 765

Ala Leu Pro Ile Asn Ala Leu Thr Asp Thr Pro Val Val Tyr Asn Asp
770                 775                 780

Ala Asn Ala Ser Gly Gly Lys Lys Leu Gly Phe Asn Asn Ala Val
785                 790                 795                 800

Asp Asp Tyr Val Glu Phe Ser Leu Asp Val Thr Gln Pro Gly Thr Tyr
                805                 810                 815

Asp Val Lys Ser Arg Ile Met Lys Ser Thr Asn Ser Gly Ile Tyr Gln
            820                 825                 830

Leu Ser Ile Asn Gly Thr Asn Val Gly Ser Ala Gln Asp Met Phe Trp
            835                 840                 845

Thr Thr Ser Glu Leu Ser Lys Glu Phe Thr Met Gly Ser Tyr Ser Phe
850                 855                 860

Ser Thr Pro Gly Ser Tyr Leu Phe Arg Leu Lys Thr Thr Gly Lys Asn
865                 870                 875                 880

Val Ser Ser Ser Gly Tyr Lys Leu Met Leu Asp Asn Phe Ser Leu Val
                885                 890                 895

Ser Thr Gly Ile Asp Thr Thr Val Ile Val Asp Asn Ala Asp Ala Ala
            900                 905                 910

Gly Val Thr Lys Val Gly Thr Trp Thr Gly Thr Asn Thr Gln Thr Asp
            915                 920                 925

Arg Tyr Gly Ala Asp Tyr Ile His Asp Gly Asn Thr Gly Lys Gly Thr
            930                 935                 940

Lys Ser Val Thr Phe Thr Pro Asn Val Pro Ile Ser Gly Thr Tyr Gln
945                 950                 955                 960

Val Tyr Met Met Trp Ala Ala His Thr Asn Arg Ala Thr Asn Val Pro
                965                 970                 975

Val Asp Val Thr His Ser Gly Gly Thr Ala Thr Leu Asn Val Asn Gln
            980                 985                 990

Gln Gly Asn Gly Gly Val Trp Asn Leu Leu Gly Thr Tyr Ser Phe Asn
            995                 1000                1005

Ala Gly Ser Thr Gly Ala Ile Lys Ile Arg Thr Asp Ala Thr Asn
    1010                1015                1020

Gly Tyr Val Val Ala Asp Ala Val Lys Leu Val Lys Val Pro
    1025                1030                1035